(12) United States Patent
Patankar et al.

(10) Patent No.: US 8,492,104 B2
(45) Date of Patent: Jul. 23, 2013

(54) METHODS AND KITS TO DETECT AND MONITOR OVARIAN CANCER AND PREECLAMPSIA

(75) Inventors: Manish S. Patankar, Fitchburg, WI (US); Joseph P. Connor, Madison, WI (US); Jennifer A. Belisle, De Forest, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/454,276

(22) Filed: Apr. 24, 2012

(65) Prior Publication Data
US 2012/0264140 A1    Oct. 18, 2012

Related U.S. Application Data

(62) Division of application No. 12/429,573, filed on Apr. 24, 2009, now Pat. No. 8,187,801.

(60) Provisional application No. 61/047,660, filed on Apr. 24, 2008.

(51) Int. Cl.
*G01N 33/53* (2006.01)

(52) U.S. Cl.
USPC .......................................................... 435/7.1

(58) Field of Classification Search
None
See application file for complete search history.

(56) References Cited

PUBLICATIONS

Tockman et al (Cancer Res., 1992, 52:2711s-2718s).*
Zhang et al (JBC, 2000, 275: 22121-22126).*
Connor et al., CA125 (MUC16): Not Just a Marker Anymore, PowerPoint Presentation, Mar. 17, 2005 UWCCC Grand Rounds Seminar.
Tumor Immunology Journal Club, The Ovarian Tumor Mucin, MUC16: A Slimy Character, PowerPoint Presentation, Nov. 22, 2005.
Belisle et al., Phenotypic and Functional Analysis of Natural Killer Cells in Patients with Epithelial Ovarian Cancer, 2006 SGO abstract.
Arens et al., Cell Surface Expression of MUC16 Prevents Effective Lysis of OVCAR-3 Cells by the Natural Killer (NK) Cell Leukemia Cell Line, NKL—A Model to Study NK Cell Dysfunction in Ovarian Cancer Patients, 2006 SGO abstract.
Arens et al., Mesothelin Bins to the Oligosaccharides Expressed on MUC16 to Promote Peritoneal Metastasis of Ovarian Tumors, 2006 SGO abstract.
Belisle et al., Phenotypic Analysis of Natural Killer Cells in Patients with Epithelial Ovarian Cancer, 2007 SGI abstract.
Patankar, Biological Roles of the Ovarian Tumor Marker MUC16 (CA125): Update and Future Directions, PowerPoint Presentation, Perinatal Group Seminar—Jan. 9, 2007.
Belisle at al., The Role of the Ovarian Tumor Marker CA125 (MUC16) in the Suppression of Human Immune Response, 2005 ISBTC poster.
Hebda at al., Phenotypic and Functional Analysis of Natural Killer Cells in Patients with Epithelial Ovarian Cancer, 2005 UW Immunology Symposium abstract.
Belisle et al., Peritoneal Natural Killer Cells from Epithelial Ovarian Cancer Patients Show an Altered Phenotype and Bind to the Tumour Marker MUC16 (CA125), 2007, Immunology 122:418-429.

* cited by examiner

*Primary Examiner* — Sean Aeder
(74) *Attorney, Agent, or Firm* — Quarles & Brady LLP

(57) ABSTRACT

The present invention provides methods and kits related to a prognostic, and, in certain embodiments, diagnostic indicator for ovarian cancer which comprises measuring the level of MUC16 bound to immune cells. The level of MUC16 bound to immune cells can by itself be an indicator of disease regression or recurrence, or this indicator can be used in conjunction with assays for serum CA125 and other diagnostic markers. The invention further provides methods and kits related to the detection of ovarian cancer by measuring levels of Siglec-9 expression on immune cells. As well, related methodologies are provided for the detection of preeclampsia in pregnant human subjects.

3 Claims, 17 Drawing Sheets

METHODS AND KITS TO DETECT AND MONITOR OVARIAN CANCER AND PREECLAMPSIA

CROSS-REFERENCE TO RELATED APPLICATION

This application is a divisional application of U.S. patent application Ser. No. 12/429,573, filed Apr. 24, 2009, which claims the benefit of U.S. Provisional Application Ser. No. 61/047,660, filed Apr. 24, 2008. All applications are incorporated herein by reference as if set forth in their entirety.

STATEMENT REGARDING FEDERALLY SPONSORED RESEARCH OR DEVELOPMENT

This invention was made with government support under W81XWH-04-1-0102 awarded by the ARMY/MRMC. The government has certain rights in the invention.

FIELD OF THE INVENTION

This invention relates generally to biochemical assays in the field of medicine. In particular, this invention is directed to methods and related materials for detecting and monitoring the progression of ovarian cancer in human subjects and, by related methodology, preeclampsia in pregnant subjects.

BACKGROUND OF THE INVENTION

A majority of human epithelial ovarian tumors express elevated levels of the antigen CA125. This antigen is a repeating peptide epitope located on the mucin MUC16. Elevations in the serum concentration of CA125 are routinely determined in order to monitor the progression of epithelial ovarian cancer in patients undergoing treatment for this disease.

MUC16 is a mucin with an average molecular weight of 5 million Da. Contributing to this high molecular weight of MUC16 are the over 22,000 amino acids that make up the protein backbone and the extensive N-linked and O-linked oligosaccharide chains. This mucin is cell surface bound mucin and expressed on the ovarian, endometrial, and ocular surface epithelial cells. Cell surface bound MUC16 (cs-MUC16) carries an extensive N-terminal epitope followed by approximately 60 tandem repeats that are each composed of 156 amino acids. A transmembrane segment attaches the mucin to the cell surface and is followed by a short cytoplasmic tail. Proteolytic cleavage at a site upstream of the transmembrane segment results in shedding of MUC16 from the cell surface. The shed MUC16 (sMUC16) is released in the peritoneal fluid (PF) of ovarian cancer patients or may leak into the systemic circulation where it can be detected by using the serum CA125 assay.

It was recently shown that natural killer (NK) cells isolated from the peripheral blood (PB) and the PF of ovarian cancer patients are recognized by anti-MUC16 antibodies. RT-PCR and other in vitro experiments demonstrate that the NK cells do not synthesize this mucin but instead acquire the sMUC16 that is shed from the ovarian cancer cells. Even though the amount of sMUC16 in the PB of ovarian cancer patients is 10-100-fold lower than the PF, robust amounts of sMUC16 were detected on the NK cells in peripheral circulation.

At present, CA125 is a widely utilized biomarker for ovarian cancer. CA125 levels in serum do rise in ovarian cancer, but also in pregnancy and endometriosis. Even though CA 125 is not specific for ovarian cancer, it has proven to be useful as a prognostic after diagnosis and therapy for monitoring for recurrence of disease. After treatment, the baseline level of CA 125 achieved is somewhat prognostic for timeframe to tumor recurrence. CA125 levels up to 35 U/ml are considered normal, while levels over two times this amount are considered abnormal. Several publications link the production of MUC16 to a suppression of immune response in the host as well as to tumor metastasis in the peritoneal cavity.

Unfortunately, CA125 assays give high levels of false positives, making this a poor screening tool for the general population. In addition, CA125 levels may also rise in alcoholic liver disease, pleurisy, and bronchitis. Therefore, the reliability of this marker in terms of sensitivity and specificity is not entirely satisfactory. An improved biomarker with better diagnostic capability is desperately needed in the art.

SUMMARY OF THE INVENTION

Accordingly, the invention provides in a first aspect a method to detect ovarian cancer in a subject. Such a method includes steps of: (a) obtaining a sample of immune cells from a subject; and (b) measuring the sample of immune cells from the subject for MUC16 bound to immune cells contained in the sample, wherein an elevated level of MUC16 bound to the immune cells indicates ovarian cancer in the subject. The immune cell sample is preferably a peripheral blood, peritoneal fluid, or tissue sample.

In certain embodiments, an antibody specific for MUC16 is used to measure the level of MUC16 bound to the immune cells and the level of MUC16 bound to the immune cells is determined by flow cytometry detection of the antibody specific for MUC16. Detection of the immune complex comprising the antibody specific for MUC16 and MUC16 bound to the immune cells may be carried out by radioisotopic, enzymatic, fluorogenic, chemiluminescent, or electrochemical means.

In certain embodiments, the method is repeated at least once with said subject in order to monitor the progress of ovarian cancer in the subject.

It is preferred that step (b) of measuring MUC16 bound to immune cells is based on immune cells selected from Siglec-9 expressing natural killer cells, B cells, monocytes, neutrophils, or mixtures thereof contained within the sample. In particular, step (b) preferably measures the binding of MUC16 to natural killer cell subsets $CD16^{pos}/CD56^{dim}$ and $CD16^{neg}/CD56^{bright}$ present in the immune cells contained within the sample in order to obtain a distribution of MUC16 between said subsets. An elevated level of MUC16 bound to the $CD16^{neg}/CD56^{bright}$ subset as compared to the $CD16^{pos}/CD56^{dim}$ subset indicates ovarian cancer in the subject. The level of MUC16 bound to the $CD16^{neg}/CD56^{bright}$ subset is preferably elevated by at least 2 fold as compared to the $CD16^{pos}/CD56^{dim}$ subset in order to be indicative of ovarian cancer.

In another aspect, the invention provides yet another method to detect ovarian cancer in a subject. Such a method includes steps of: (a) obtaining a sample of immune cells from a subject; and (b) measuring the sample of immune cells from the subject for Siglec-9 expressed on immune cells contained in the sample, wherein an elevated level of Siglec-9 bound to the immune cells indicates ovarian cancer in the subject.

In certain embodiments, an antibody specific for Siglec-9 is used to measure the level of Siglec-9 expressed on the immune cells and the level of Siglec-9 expressed on the immune cells is determined by flow cytometry detection of the antibody specific for Siglec-9. Detection of the immune complex comprising the antibody specific for Siglec-9 and Siglec-9 expressed on the immune cells may be carried out by radioisotopic, enzymatic, fluorogenic, chemiluminescent, or electrochemical means.

In certain embodiments, the method is repeated at least once with said subject in order to monitor the progress of ovarian cancer in the subject.

It is preferred that step (b) of measuring Siglec-9 expressed on the immune cells is based on immune cells selected from Siglec-9 expressing natural killer cells, B cells, monocytes, neutrophils, or mixtures thereof contained within the sample. In particular, step (b) preferably measures the expression of Siglec-9 on natural killer cell subsets $CD16^{pos}/CD56^{dim}$ and $CD16^{neg}/CD56^{bright}$ present in the immune cells contained within the sample in order to obtain a distribution of Siglec-9 between said subsets. An elevated level of Siglec-9 expressed on the $CD16^{neg}/CD56^{bright}$ subset as compared to the $CD16^{pos}/CD56^{dim}$ subset indicates ovarian cancer in the subject.

In yet another aspect, the invention is directed to a method to detect preeclampsia in a pregnant subject. Such a method includes steps of: (a) obtaining an immune cell sample from a pregnant subject; and (b) measuring expression of Siglec-9 on natural killer cell subsets $CD16^{pos}/CD56^{dim}$ and $CD16^{neg}/CD56^{bright}$ contained within the immune cell sample in order to obtain a distribution of Siglec-9 between the subsets, wherein a higher level of Siglec-9 on the $CD16^{neg}/CD56^{bright}$ subset as compared to the $CD16^{pos}/CD56^{dim}$ subset indicates preeclampsia in the pregnant subject. It is preferable that the level of Siglec-9 on the $CD16^{neg}/CD56^{bright}$ subset is at least 1.5 fold higher than the Siglec-9 on the $CD16^{pos}/CD56^{dim}$ subset to be indicative of the preeclampsic condition. Furthermore, the immune cell sample is preferably a peripheral blood sample.

In a further aspect, the invention encompasses another method to detect preeclampsia in a pregnant subject. Such a method includes steps of: (a) obtaining an immune cell sample from a pregnant subject; and (b) measuring binding of MUC16 to natural killer cell subsets $CD16^{pos}/CD56^{dim}$ and $CD16^{neg}/CD56^{bright}$ contained within the immune cell sample in order to obtain a distribution of MUC16 between said subsets, wherein a higher level of MUC16 bound to the $CD16^{neg}/CD56^{bright}$ subset as compared to the $CD16^{pos}/CD56^{dim}$ subset indicates preeclampsia in the pregnant subject. It is preferable that the level of MUC16 bound to the $CD16^{neg}/CD56^{bright}$ subset is at least 2 fold higher than the MUC16 bound to the $CD16^{pos}/CD56^{dim}$ subset. Also, the immune cell sample is preferably a peripheral blood sample.

The invention further encompasses kits containing reagents which facilitate methods of detecting and monitoring ovarian cancer in a subject. Such kits include, for example: an anti-MUC16 antibody, labeled, if required; reagents to create a medium favorable to the immunological reaction between the anti-MUC16 antibody and MUC16 bound to immune cells within a biological sample or specimen; one or more reagents labeled, if required, capable of reacting with the anti-MUC16 antibody, or conjugates/immune complexes of the anti-MUC16 antibody and immune cell bound MUC16, to detect the conjugates/immunological complexes possibly formed; if applicable, a control and/or reference sample or biological medium. An alternative or additional antibody for inclusion in a kit to detect and monitor ovarian cancer is an anti-Siglec-9 antibody. Exemplary reference samples may be peripheral blood samples of patients showing three levels of assay results, previously correlated to clinical outcome: low ovarian cancer risk; moderate ovarian cancer risk; and strong ovarian cancer risk.

Additional kits encompassed by the invention facilitate methods of identifying preeclampsia in a pregnant subject. Such kits include, for example: an anti-MUC16 antibody, labeled, if required; reagents to create a medium favorable to the immunological reaction between the anti-MUC16 antibody and MUC16 bound to immune cells within a biological sample or specimen; one or more reagents labeled, if required, capable of reacting with the anti-MUC16 antibody, or conjugates/immune complexes of the anti-MUC16 antibody and immune cell bound MUC16, to detect the conjugates/immunological complexes possibly formed; if applicable, a control and/or reference sample or biological medium. An alternative or additional antibody for inclusion in a kit to detect preeclampsia is an anti-Siglec-9 antibody. Exemplary reference samples may be peripheral blood samples of patients showing various levels of assay results, previously correlated to clinical outcome. The kits may further include instructional materials such as booklets and/or electronic media which describe use of the reagents, assay steps via, for example, flow cytometry, and/or interpretation of assay results.

Other objects, features and advantages of the present invention will become apparent after review of the specification, claims and drawings.

DETAILED DESCRIPTION OF THE INVENTION

Figure 1:
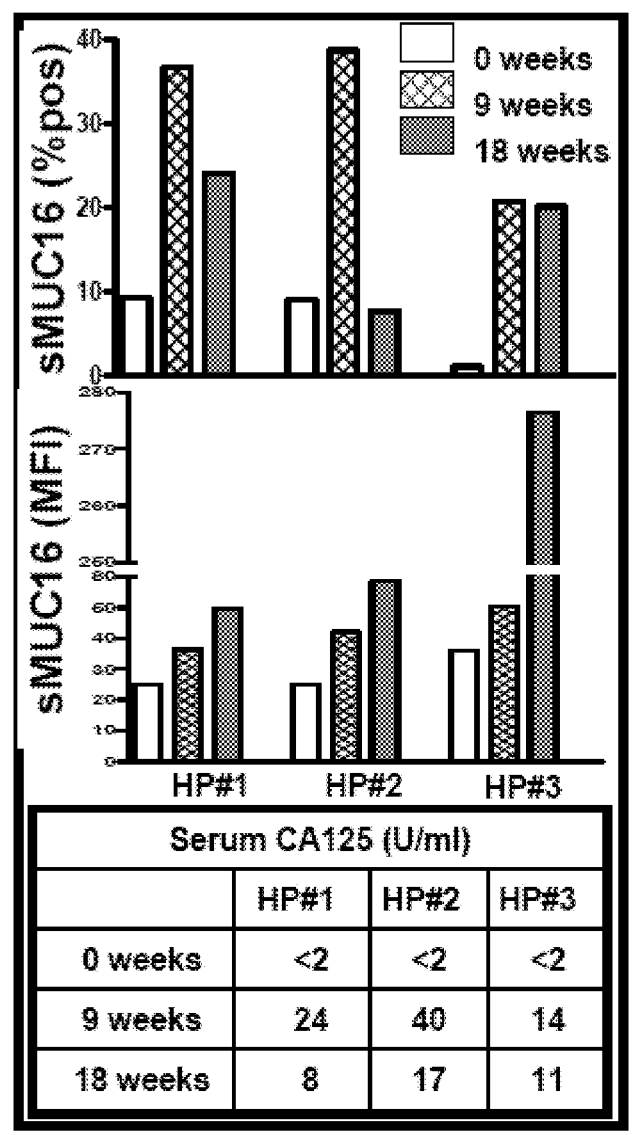
FIG. 1. sMUC16 binds to NK cells during pregnancy. PB mononuclear cells from three pregnant women at weeks 0, 9 and 18 of pregnancy were analyzed by flow cytometry. Percent of $sMUC16^{pos}$ NK cells (upper panel) and amount (lower panel) of sMUC16 on these cells (MFI) was determined. The NK cells were identified by using a fluorophore conjugated anti-CD3, CD16, CD45, CD56, and NKp46 antibody panel. Serum samples were drawn from the donors at the same time when the mononuclear cells were isolated. The serum CA125 levels were determined by the clinical assay.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention that will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986).

As used herein, the term "immune cell" shall generally refer to white blood cells that help to defend the body against infectious disease and foreign materials as part of the immune system. Methods according to the present invention utilize immune cells which are white blood cells including, but not limited to, natural killer (NK) cells, B cells, monocytes/macrophages, and neutrophils, that express Siglec-9. Immune cells may be collected from human subjects (also termed "patients") by a variety of techniques known in the art including those described in specific examples below, and as generally described at, e.g., Garza, D. and Becan-McBride, K. Phlebotomy Handbook: Blood Collection Essentials, Prentice Hall (2004).

The present invention is related to the inventors' determination that levels of MUC16 bound to immune cells provide an improved indicator of disease regression and recurrence as compared to widely utilized serum CA125 assays. More specifically, the inventors have demonstrated that MUC16 binds to NK cells and, based on analyses of blood samples from ovarian cancer patients, a restricted subset of B cells and a majority of the monocytes. The inventors have further observed that MUC16 levels rise in pregnant women, but before pregnancy these same women have undetectable levels of MUC16 on their immune cells and no detectable serum CA125 levels. In the first trimester of pregnancy, the serum CA125 levels rise to around 20-50 U/ml and MUC16 binding to the immune cells shows a similar rise. However, in the second trimester when serum CA125 levels are less than 20 U/ml, high amounts of MUC16 continue to be detected on the immune cells. It therefore is possible to detect MUC16 on the immune cells even when the concentration of CA125 in serum cannot be ascertained. The level of MUC16 on the immune calls can by itself be an indicator of disease regression or recurrence, or these results can be used in conjunction with serum CA125 and other diagnostic markers. Accordingly, the present invention provides a prognostic, and, in certain embodiments, a diagnostic indicator for ovarian cancer which comprises measuring the MUC16 (CA125) bound to immune cells rather than or in addition to CA125 in serum.

Ovarian tumors and epithelial cells of the ovary, endometrium, and decidual cells express MUC16 on their cell surface. This cell surface bound MUC16 is referred to as "csMUC16." The csMUC16 is released from the surface of these respective cells following proteolytic cleavage. The shed MUC16 is referred to as "sMUC16." The sMUC16 is present in high amounts in the peritoneal fluid that surrounds ovarian tumors and sMUC16 subsequently leaks into the peripheral blood.

MUC16 significantly contributes to the pathophysiology of ovarian tumors. First, spread of the ovarian tumor cells in the peritoneum is facilitated by the interaction between csMUC16 and mesothelin, a glycoprotein expressed on the mesothelial cells lining the peritoneal walls and the internal organs. Second, sMUC16 is a potent inhibitor of the cytolytic responses of human NK cells. The NK cells derived from the PB of healthy donors when incubated with sMUC16 isolated from the ovarian tumor cell line, OVCAR-3, undergo a reduction in CD16 and are severely inhibited in their ability to lyse K562 target cells. Since sMUC16 binds to the NK cells from ovarian cancer patients, it is likely that this mucin may be recognized by inhibitory receptor(s) on the NK cells. Thus sMUC16 may serve as a strategy employed by the ovarian cancer cells to evade immune recognition.

Given the potential importance of the interaction between sMUC16 and the NK cells for diagnostic purposes and also to understand the immunosuppressive effects of sMUC16 the inventors conducted experiments to identify the inhibitory receptor for sMUC16 on the human NK cells.

As noted above, the ovarian tumor marker CA125 is a repeating peptide epitope expressed on the mucin MUC16. This mucin binds to the surface of human natural killer (NK) cells. The present inventors have now examined immune cells from ovarian cancer patients, healthy donors and pregnant women and monitored MUC16 and a panel of cell markers by flow cytometry. Western blotting and other techniques were then utilized to identify the receptor for MUC16 on the immune cells. MUC16 was detected on the immune cells of pregnant women even when the levels of CA 125 in the serum were very low or undetectable. In ovarian cancer patients, sMUC16 was present on $CD16^{pos}/CD56^{dim}$ NK cells, subsets of $CD19^{pos}$ B cells and >90% of the monocytes. While no one specific mechanism of action is adopted herein, the inventors' results indicated that binding was mediated via the recognition of the sialic acid residues expressed on MUC16 by the I-type lectin receptor Siglec-9. The amount of MUC16 and its retention on the immune cells was correlated with the expression levels of Siglec-9 on the immune subsets. It was determined that MUC16, in the form of sMUC16, was captured on the immune cells while the free mucin in the serum was apparently undergoing rapid hepatic uptake and degradation. Accordingly, the inventors determined that assays to identify immune cell bound sMUC16 provided novel diagnostic methods that are useful to monitor ovarian cancer progression.

A majority of the patients with epithelial ovarian tumors express MUC16. This mucin is detected in the serum of patients as the tumor antigen CA125. Because the levels of serum CA125 are higher in pregnant women and in endometriosis, liver cirrhosis and breast cancer patients, this marker cannot be used for early detection of epithelial ovarian cancer. Instead, serum CA125 levels are routinely monitored in patients who are already undergoing treatment for ovarian cancer. A decrease in serum CA125 indicates a positive response to the treatment regimen whereas, increase in this marker above a nadir concentration suggests recurrence of the tumor.

One major factor that impacts efficient detection of CA125 (MUC16) and other mucinous cancer antigens in the sera is their degradation by the liver. Circulating mucins are rapidly cleared by the hepatic reticuloendothelial cells. Tritium labeled tracer mucins injected in mice have a serum half-life of ~1 min. This clearance of the mucins occurs via the involvement of galactose, mannose/N-acetylgalactosamine-4-sulfate, hyaluronan receptors and the scavenger receptors. Only a small susbset of the total mucin has a higher half-life and persist in the sera. These isoforms of the mucins that resist rapid hepatic uptake constitute the molecules that can be detected using the conventional serum CA125, CA19-9, CA15-3 and other assays. The hepatic uptake of mucins therefore hampers efficient detection of these tumor antigens in cancer patients.

The inventors have demonstrated that immune cells from ovarian cancer patients are decorated with sMUC16. A similar binding of sMUC16 was also observed on the NK cells from pregnant women. Fluctuations in amount of sMUC16 bound to the NK cells and the percentage of total NK cells positive for this mucin vary significantly in pregnant women monitored at 0, 9 and 18 weeks of pregnancy (FIG. 1). More importantly, sMUC16 could be identified (either by measuring the total percentage of mucin positive NK cells or by mean fluorescence intensity, or both) on the NK cells from pregnant women even when the serum levels of CA125 were undetectable.

Based on these observations, the inventors determined that monitoring the NK cell bound sMUC16 provides an alternate, and a more sensitive method for detecting the regression and recurrence of ovarian cancer in women who are undergoing treatment for this disease.

Figure 2:
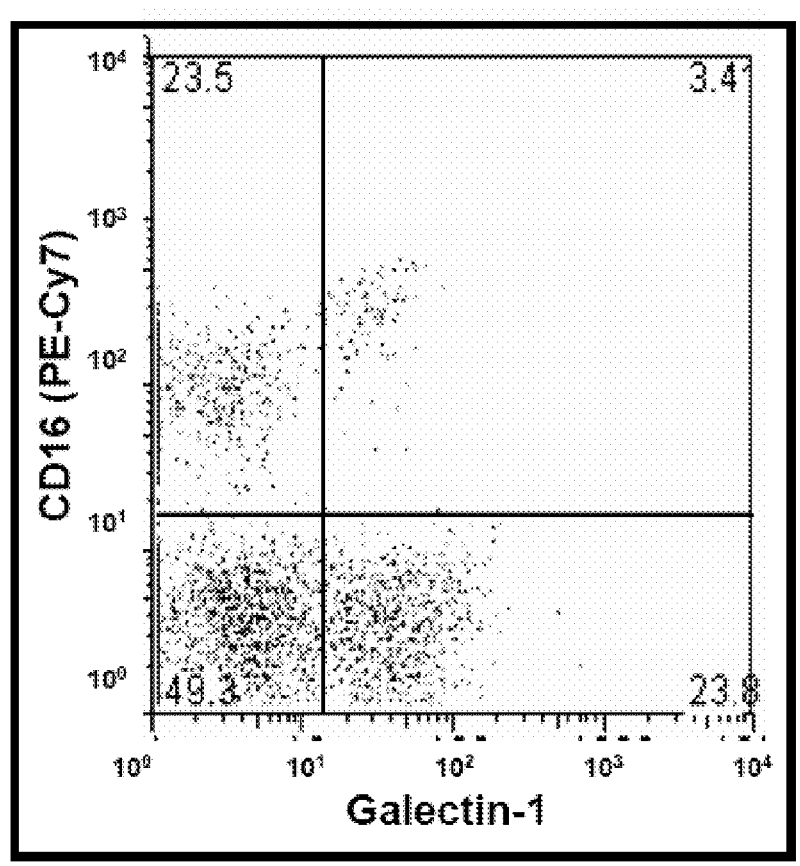
FIG. 2. Galectin-1 expression profile on NK cell subsets. The PB mononuclear cells were isolated from healthy donors. The cells were stained with a panel of fluorophore conjugated anti-CD3, CD16, CD45, CD56, and unconjugated galectin-1 antibodies. Galectin-1 binding was detected by FITC-labeled goat anti-mouse secondary antibody. Cells were analyzed by flow cytometry. Live, single events were analyzed. The expression of galectin-1 on $CD16^{pos}$ subsets which were $CD56^{dim}$ is shown. Data shown is for NK cells from HD#25 and is representative of results obtained from three healthy donors.

The extensive protein backbone and the dense glycosylation of MUC16 suggests that this mucin mediates various important biological processes. The sMUC16 isolated from OVCAR-3 cells is a potent inhibitor of NK cell function and subsets of NK cells from the PB and PF of ovarian cancer patients carry this mucin on their surface. Based on previous reports the inventors initially hypothesized that sMUC16 binding to the immune cells may occur via its interaction with galectin-1. However, the NK cell subsets that are positive for galectin-1 do not exhibit any binding to sMUC16 (FIG. 2). The inventors therefore investigated other NK cell receptors as binding counterparts for sMUC16.

Considering the heavy glycosylation of MUC16, the inventors decided to initially only focus on the NK receptors that carried lectin domains. Furthermore, since sMUC16 attenuated NK cell function the inventors narrowed their search only to inhibitory NK cell receptors. Using these criteria the inventors excluded the ITIM bearing inhibitory Killer Immunoglobulin-like Receptors (KIR), because their ligands are HLA Class-I antigens, and the activating natural cytotoxicity receptors (NKp30, NKp44, and NKp46) as the potential binding partners for sMUC16. Although NKG2D carries a lectin domain, this receptor was not considered since it is an activating molecule. The inhibitory heterodimeric receptor CD94/NKG2A was also not considered since its ligands have been well demonstrated in past studies.

Human NK cells express the CD33-like Siglec-7 and Siglec-9. Both these receptors carry an ITIM motif in their cytoplasmic tails and are known to inhibit immune responses. The Siglecs recognize terminal sialic acid epitopes via their I-type lectin domains. The inventors therefore considered Siglec-7 and Siglec-9 as the potential receptors for sMUC16 on the NK cell surface.

Figure 3:
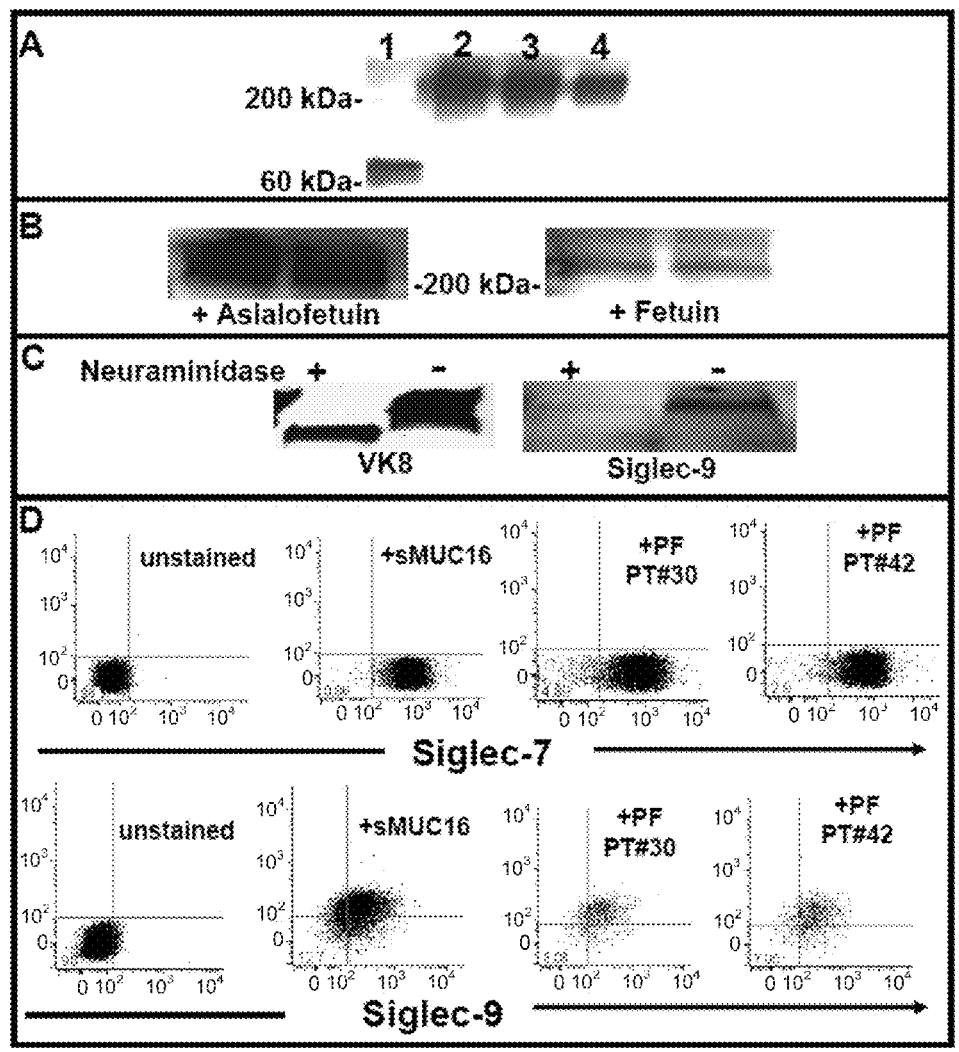
FIG. 3. Siglec-9 binds to sialylated glycans of sMUC16. A, Fetuin (lane 1) or sMUC16 (300 U of CA125, lane 2; 200 U of CA125, lane 3; and 100 U of CA125, lane 4) were separated by SDS-PAGE, transferred to a PVDF membrane and overlaid with Siglec-9-human Fc chimera (0.2 µg/ml). Binding of Siglec-9-human Fc was detected using horseradish peroxidase labeled mouse anti-human Fc secondary antibody. B, sMUC16 (250 U of CA125/lane) purified from the spent media of OVCAR-3 cells was loaded in duplicate on both the blots. Binding of Siglec-9-human-Fc chimera to the sMUC16 was detected in the presence of 3-fold molar excess of asialofetuin or fetuin. C, sMUC16 was desialylated with neuraminidase from *Clostridium perfringens*. Binding of neuraminidase treated and untreated sMUC16 samples (250 U of CA125/lane) to VK-8 (left panel) or Siglec-9-human-Fc (right panel) was detected by western blotting. D, Siglec-7 (top panel) and Siglec-9 (bottom panel) expressing Jurkat cells were incubated for 24 h in media, media containing OVCAR-3 derived sMUC16 (50,000 U of CA125/ml), or in 10% media containing 90% PF from ovarian cancer patients (PT #30 and PT #42). The VK-8 antibody was used to detect binding of sMUC16 to the cells by flow cytometry.

Although both Siglec-7 and Siglec-9 recognize terminal sialic acid residues they differ in their ligand specificities. Siglec-7 preferentially binds to 2-8-linked sialic acid residues that are not expressed on sMUC16. On the other hand, Siglec-9 recognizes 2-3 linked sialic acid residues that are also expressed on the O-linked as well as the N-linked glycans of sMUC16. The inventors' initial western blot analysis clearly indicated that Siglec-9 could bind to sMUC16 in a sialic acid dependent manner (FIG. 3A-C). Additional cell surface binding experiments proved that sMUC16 could bind only to the Jurkat cells that expressed Siglec-9 and not to those expressing Siglec-7 (FIG. 3D).

Figure 4:
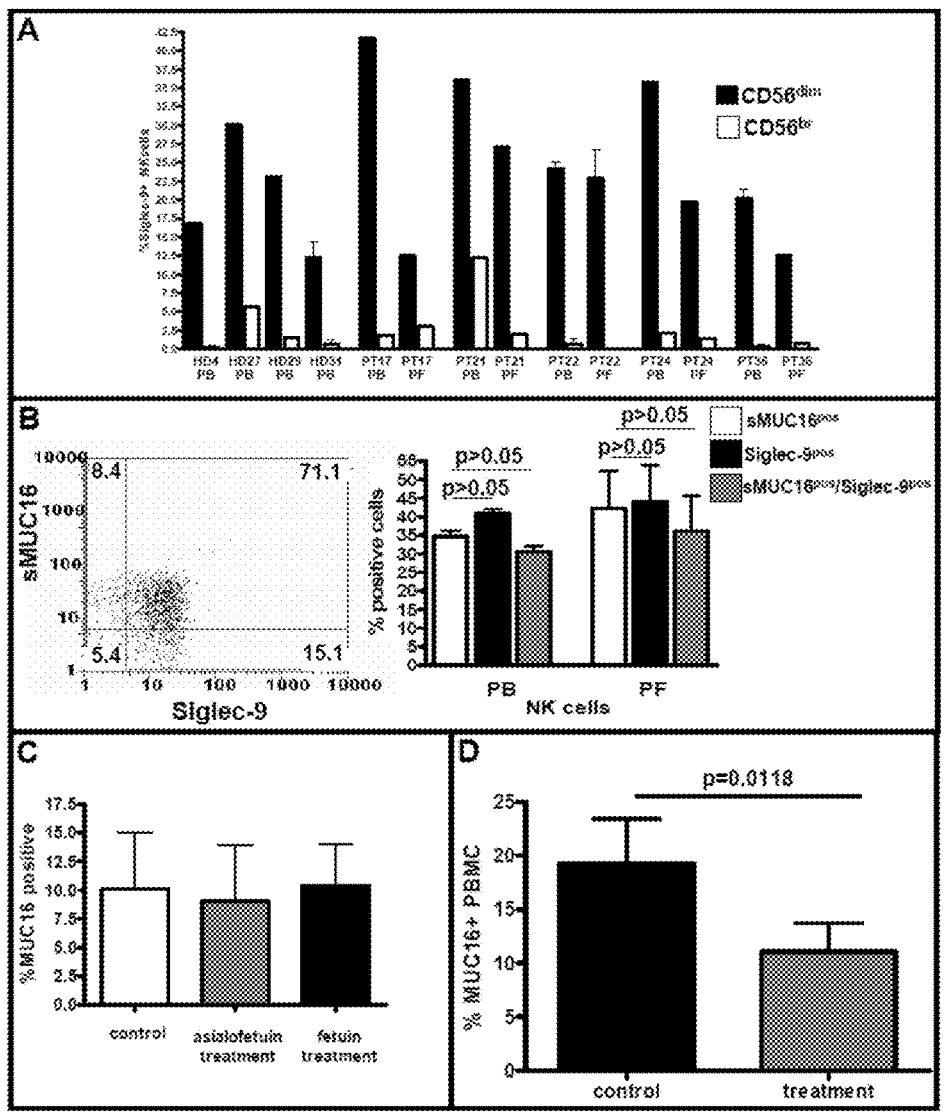
FIG. 4. sMUC16 predominantly binds to Siglec-9$^{pos}$ NK cells of ovarian cancer patients. A, NK cells from the PB and PF of ovarian cancer patients were labeled with anti-Siglec-9 antibody to determine expression of this lectin on the CD16$^{pos}$/CD56$^{dim}$ (CD56$^{dim}$) and CD16$^{neg}$/CD56$^{br}$ (CD56$^{br}$) subsets. Distribution of Siglec-9 on the NK cell subsets from the PB of four healthy donors (HD) is also shown. Each bar represents a mean of three independent experiments. B, The expression of Siglec-9 and presence of bound sMUC16 on the NK cells obtained from the PB of PT#36 is shown in the left panel. The NK cells from the PB and PF of six ovarian cancer patients were analyzed by flow cytometry for sMUC16 and Siglec-9. Average percentage of the cells positive for sMUC16 or Siglec-9 and those positive for both these markers is plotted in the panel on the right. C, The mononuclear cells from the PB of three ovarian cancer patients (PT#17, PT#21, and PT#22) were incubated in media only (Control) or with 1 mg/ml of asialofetuin or fetuin. Following incubation the cells were stained with VK-8 and fluorophore conjugated anti-CD3, CD16, CD45, and CD56 antibodies to monitor sMUC16 levels on the NK cells. D, PB mononuclear cells from six ovarian cancer patients were individually incubated in PBS-BSA or in PBS-BSA containing neuraminidase from *Clostridium perfringens*. After 15 min incubation at room temperature, the cells were washed and stained with antibodies to determine sMUC16 binding to NK cells by flow cytometry.
Figure 5:
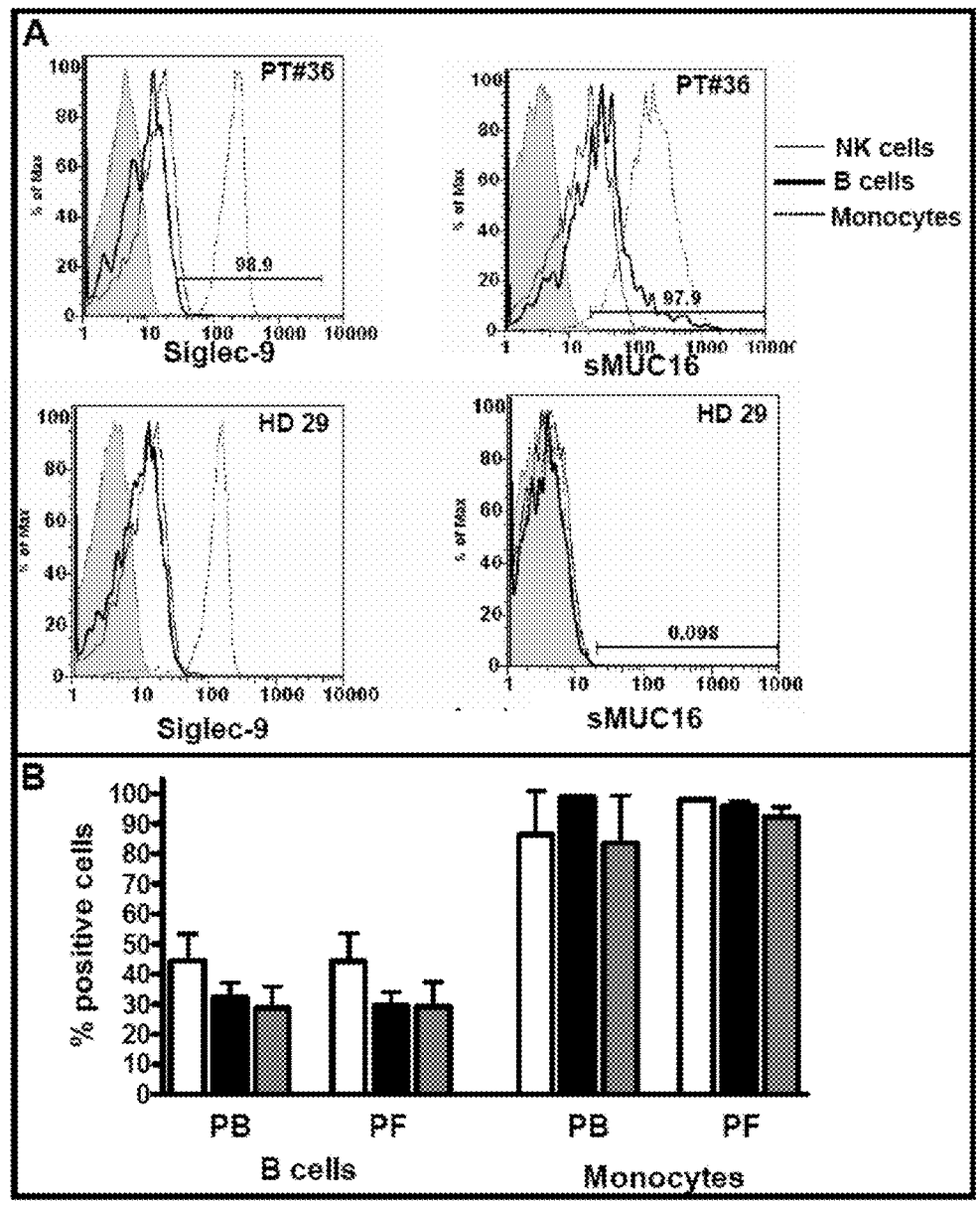
FIG. 5. sMUC16 is present on B cells and monocytes. A, The mononuclear cells from the PB of PT#22, PT#24, PT#36 (plotted) and HD#4, HD#29 (plotted), HD#31 were isolated and labeled with VK-8, and fluorophore conjugated anti-CD3, CD16, CD19, CD33, CD45, CD56, and Siglec-9 antibodies and analyzed by flow cytometry. Expression of Siglec-9 and presence of bound sMUC16 is shown. B, Composite data on the expression of Siglec-9 and the presence of bound sMUC16 on the B cells and monocytes of three ovarian cancer patients tested in duplicate (PT#22, PT#24, PT#36) is plotted.

Siglec-9 is not expressed on all of the PB derived human NK cells but only on 15-30% of the $CD16^{pos}/CD56^{dim}$ subsets (FIG. 4A). The PB and the PF NK cells that bind sMUC16 also have the $CD16^{pos}/CD56^{dim}$ phenotype. Careful analysis clearly showed that only those patient derived NK cells that were positive for Siglec-9 were the ones that bound sMUC16 (FIG. 4B). Apart from the NK cells Siglec-9 is also expressed on a subset of the $CD19^{pos}$ B cells and greater than 90% of all monocytes (FIG. 5A,B). The B cells and monocytes isolated from the PB and PF of ovarian cancer patients also carried bound sMUC16 on their surface (FIG. 5A,B). Siglec-9 is also expressed on neutrophils. Based on current results the inventors predict that $Siglec-9^{pos}$ neutrophils from ovarian cancer patients also carry sMUC16 on their cell surface.

Figure 6:
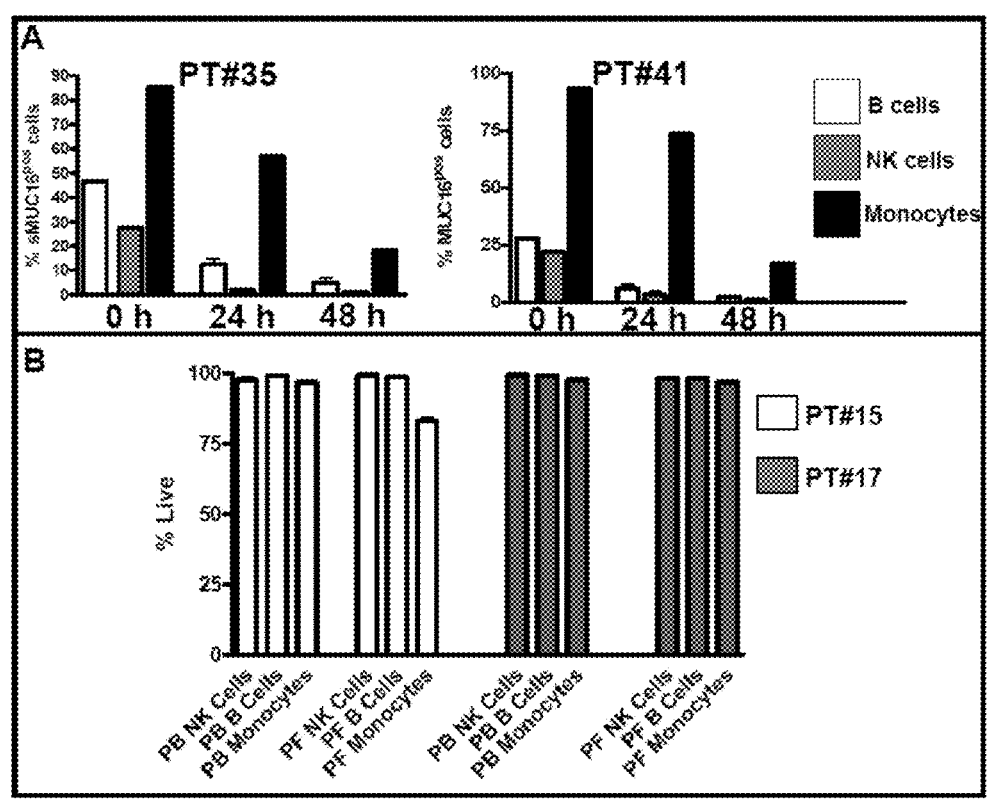
FIG. 6. sMUC16 is preferentially retained on the monocytes and does not cause cell death of the immune cells. A, Mononuclear cells from the PB of two ovarian cancer patients were washed in PBS-BSA and cultured in RPMI 1640 containing 10% fetal calf serum for 0, 24, and 48 h. Following incubation, the cells were labeled with VK-8, and fluorophore conjugated anti-CD3, CD16, CD19, CD33, CD45, and CD56 antibodies. The percentage of cells positive for sMUC16 under the experimental conditions was determined by flow cytometry. B, The NK cells, B cells, and monocytes from the PB of two ovarian cancer patients were analyzed for cell death using DAPI.

The monocytes express significantly high amounts of Siglec-9 on their surface and also greater than 95% of these cells are positive for this lectin receptor (FIG. 5A,B). Consequently, the monocytes also exhibit a very high capacity for binding sMUC16 as compared to the NK cells or the B cells. The monocytes in in vitro cultures also retain sMUC16 longer than the NK cells and the B cells (FIG. 6A).

As can be appreciated, continued treatment with chemotherapeutic agents until levels of sMUC16 on monocytes have reached a nadir provides an effective method for monitoring ovarian cancer progression. Thus, a diagnostic test according to the invention benefits from simultaneously monitoring the sMUC16 levels on the individual immune cell subsets and correlating the data with clinical outcomes.

Stimulation with anti-Siglec-9 results in apoptotic death of neutrophils and this effect is enhanced following cytokine stimulation. The inventors have not observed any increase in death of sMUC16 bound NK cells, B cells, or monocytes. The inventors' data indicate that sMUC16 binding to Siglec-9 may trigger a different cellular response than that generated following crosslinking with anti-Siglec-9 antibodies.

Siglec-7 was first identified as p75/AIRM1 using the Z176 antibody and shown to be an inhibitory NK cell receptor. Subsequently, Siglec-9 was shown to be expressed on a subset of NK cells. Both Siglec-7 and Siglec-9 negatively regulate T cell receptor mediated signaling. The inhibitory effects of Siglec-7 and Siglec-9 have also been demonstrated in the in vitro rat basophilic leukemia (RBL) model that has previously been used to analyze the function of the KIR's. Crosslinking of Siglec-7 or Siglec-9 with specific antibodies resulted in inhibition of FcγRI mediated degranulation of the RBL cells.

MUC16 is also observed on PB NK cells of pregnant women (FIG. 1). Since, similar to the ovarian cancer patients, the sMUC16 is primarily found on the $CD16^{pos}/CD56^{dim}$ subsets of the decidual NK cells (data not shown), it is likely that the mucin binding is occurring via Siglec-9 even during pregnancy. High levels of MUC16 are expressed in the endometrium and in the decidua. Post-implantation the NK cells are the major immune cell type observed in the decidua. The sMUC16 acting through Siglec-9 may inhibit the maternal NK cells thereby allowing appropriate development of the growing fetus. It is this mechanism of immune-modulation that seems to have been co-opted by the ovarian tumors to protect themselves from NK cell attack.

As noted above, MUC16 is also expressed by the human endometrium and decidua. CA125 levels are elevated in pregnant women and also patient with endometriosis. As described in Example 7 below, a very different profile of MUC16 binding is observed on NK cells derived from the peripheral blood of women in the third trimester of pregnancy. In this case, MUC16 is present at equal levels on both the $CD16^{pos}/CD56^{dim}$ and $CD16^{neg}/CD56^{bright}$ NK cell subsets. MUC16 binding to these NK cell subsets matches Siglec-9 expression. On the other hand, a very different MUC16 binding and a Siglec-9 expression is observed for peripheral blood NK cells isolated at term from women with preeclampsia. In this case, higher MUC16 binding and corresponding Siglec-9 expression is observed on $CD16^{neg}/CD56^{bright}$ NK cells as compared to normal pregnant women. One possible explanation is that hormonal changes occurring during pregnancy may affect Siglec-9 expression on NK and other immune cells. However, the differential Siglec-9 expression and the subsequent MUC16 binding to the two well characterized subsets of NK cells provides a method to distinguish ovarian cancer patients from healthy pregnant women and also from women with preeclampsia. It is important to note that such a distinction between patient populations is not possible by using the classical serum CA 125 test. These findings give further illustrate the advantages of the present method of monitoring immune cell bound MUC16 as diagnostic test for ovarian cancer. As can be appreciated this method relies on not only the expression of MUC16 but also its capture by specific subsets of Siglec-9 expressing immune cells.

In currently used methods, the serum CA125 levels are routinely monitored to determine the efficiency of treatment in ovarian cancer patients. While a drop and subsequent maintenance of the serum CA125 levels below 35 U/ml indicates that the chemotherapy regimen is effective, a steady increase in the levels of this marker indicate recurrence of the disease. Monitoring the MUC16 levels on immune cells according to the present invention provides a better indicator of disease regression and recurrence than the widely utilized serum CA125 assays. This assertion is partly based on the inventors' experiments with blood samples from pregnant women. In addition to ovarian cancer, MUC16 levels also rise in pregnant women. The inventors have shown that women before they become pregnant have undetectable levels of MUC16 on their immune cells, as well as undetectable serum CA125 levels. In the first trimester of pregnancy the serum CA125 levels rise to around 20-50 U/ml and a simultaneous rise in MUC16 binding to the immune cells is also observed. However, in the second trimester when the serum CA125 levels are <20 U/ml high amounts of MUC16 continue to be detected on the immune cells. The observations indicate that monitoring the levels of MUC16 on the immune cells will provide us an early snapshot of the disease prognosis in patients with ovarian cancer. Even a minor increase in tumor load in these patients may lead to detectable levels of MUC16 on the immune cells when the concentration of CA125 in the serum cannot be ascertained. This is likely because the immune cells are circulating through the lymphatic system and can act as sponges to soak up MUC16 even from isolated areas where there is active tumor growth. At this stage the amount of CA125 in the serum may be below detection limits of the currently used clinical assay.

Ovarian cancer patients undergoing treatment can be routinely tested for the levels of MUC16 on their immune cells. Accordingly, temporally spaced apart tests conducted on an individual patient facilitate the comparison of a present level of bound MUC16 to a previous level of bound MUC16 assayed at an earlier determined time point. The earlier determined level may therefore act as a predetermined threshold useful for comparative purposes on an individual subject basis. For example, if the present level is below a predetermined threshold it indicates that the patient is responding favorably to the treatment and no further therapeutic intervention may be necessary. On the other hand, when the present MUC16 level on immune cells is above the predetermined threshold it indicates that the chemotherapy is not working optimally and that the patient likely needs to be put on another therapy. Thus assay of MUC16 levels on immune cells accordingly to the invention will allow stratification of the patients into categories that will help reduce unnecessary exposure to toxic chemotherapeutic drugs or allow physicians to treat the disease more aggressively. On the other hand if a patient is responding well to treatment, she can be routinely monitored for immune cell levels of MUC16 and a rise in these values above the predetermined threshold may indicate that the disease is recurring and that therapy needs to be administered. The level of MUC16 on the immune cells can by itself be an indicator of disease regression or recurrence or these results can be used in conjunction with serum CA125 and other diagnostic markers. Therefore, this invention relates to an early cancer diagnostic process in a patient consisting of identifying by any appropriate process the level of MUC16 bound to immune cells in a biological sample obtained from such a patient.

A particularly appropriate process to assay the level of MUC16 bound to immune cells according to the invention is based on an immunological reaction between such bound MUC16 and antibodies against MUC16, or a modified form, fragment(s) or conjugate of such antibodies.

Assays according to the present invention are useful in a variety of medical settings including, but not limited to: screening a healthy population or a high risk population for the presence of ovarian cancer; making a diagnosis of ovarian cancer in a particular human patient; determining the prognosis in a particular patient; and monitoring the course in a patient in remission or while receiving surgery, radiation, or chemotherapy.

Accordingly, the invention provides in a first aspect a method to detect ovarian cancer in a subject. Such a method includes steps of: (a) obtaining a sample of immune cells from a subject; and (b) measuring the sample of immune cells from the subject for MUC16 bound to immune cells contained in the sample, wherein an elevated level of MUC16 bound to the immune cells indicates ovarian cancer in the subject.

In methods described herein, samples of immune cells are preferably in the form of a peripheral blood, peritoneal fluid, or tissue sample. In certain embodiments, immune cells are isolated from peripheral blood drawn from healthy donors or patients. In these particular methods, isolation requires layering the blood samples on a density gradient medium, centrifugation of the solution, and removal of the separated immune cells from the bulk solution by pipet or equivalent means. Such methods, as can be appreciated, require significant sample processing time and delay the actual testing of the immune cells. Alternative methods according to the invention utilize a whole blood approach and therefore significantly reduce sample processing time and delay in testing. A suitable whole blood approach is described in the next paragraph.

An exemplary method utilizing a whole blood approach includes the isolation of blood samples from ovarian cancer or preeclampsia patients, or pregnant women by using standard venipuncture techniques. A cocktail of fluorophore conjugated antibodies to identify various immune cell subsets and red blood cells is then added to the blood samples. In addition, the antibody cocktail includes fluorophore conjugated antibodies against sMUC16 and Siglec-9. The blood sample is then directly analyzed by flow cytometry where immune cell subsets bound to sMUC16 and positive for Siglec-9 are identified. The percentage of immune cells positive for sMUC16 and Siglec-9, the type of immune subsets positive for MUC16 and Siglec-9, and the mean fluorescence intensity (MFI) of sMUC16 and Siglec-9 on the immune cell subsets may then be directly determined. The information obtained from these whole blood samples is then available for the diagnosis and monitoring of ovarian cancer and preeclampsia. As can be appreciated, such an approach results in detection of MUC16 and/or Siglec-9 with very minimal preparation of the sample and is a practical method that can be easily implemented in clinical laboratories. In addition, whole blood samples in heparin or EDTA blood collection tubes received in large numbers by off site clinical laboratories may be more rapidly processed by this whole blood approach.

In certain embodiments, an antibody specific for MUC16 is used to measure the level of MUC16 bound to the immune cells and the level of MUC16 bound to the immune cells is determined by flow cytometry detection of the antibody specific for MUC16. Detection of the immune complex comprising the antibody specific for MUC16 and MUC16 bound to the immune cells may be carried out by radioisotopic, enzymatic, fluorogenic, chemiluminescent, or electrochemical means.

In certain embodiments, the method is repeated at least once with said subject in order to monitor the progress of ovarian cancer in the subject.

In the present methods, step (b) of measuring MUC16 bound to immune cells is based on immune cells selected from Siglec-9 expressing immune cells such as, e.g., the natural killer cells, B cells, monocytes, neutrophils, or mixtures thereof contained within the sample. In particular, step (b) preferably measures the binding of MUC16 to natural killer cell subsets $CD16^{pos}/CD56^{dim}$ and $CD16^{neg}/CD56^{bright}$ present in the immune cells contained within the sample in order to obtain a distribution of MUC16 between said subsets. An elevated level of MUC16 bound to the $CD16^{neg}/CD56^{bright}$ subset as compared to the $CD16^{pos}/CD56^{dim}$ subset indicates ovarian cancer in the subject. The level of MUC16 bound to the $CD16^{neg}/CD56^{bright}$ subset is preferably elevated by at least 2 fold as compared to the $CD16^{pos}/CD56^{dim}$ subset in order to be indicative of ovarian cancer.

Methods according to the invention utilize an antibody specific for MUC16 to measure the level of MUC16 bound to immune cells. In preferred embodiments, the respective antibody specific for MUC16 is a monoclonal antibody, either detectably labeled or capable of specific binding with a different antibody detectably labeled or further capable of detection. A particularly preferred anti-MUC16 antibody for use in the invention is anti-MUC16 antibody VK8. This particular antibody was provided by Dr. Beatrice Yin of the Sloan Kettering Institute, New York. This exemplary antibody was initially characterized by Dr. Yin and colleagues (Lloyd, et al. Isolation and characterization of ovarian cancer antigen CA 125 using a new monoclonal antibody (VK-8): identification as a mucin-type molecule. Int. J. of Cancer (1997).

Based on mean fluorescence intensity-based data obtained from ovarian cancer patients (see, e.g., FIG. 10B), the amount of sMUC16 bound to $CD16^{pos}/CD56^{dim}$ NK cells of ovarian cancer patients is approximately 2-6 fold higher than that found attached to the $CD16^{neg}/CD56^{bright}$ NK cell subset. Accordingly, "an elevated level of MUC16 bound to immune cells" shall refer to at least a two fold greater difference in the level of MUC16 present on the surface of the $CD16^{pos}/CD56^{dim}$ NK cell subset as compared to that present on the $CD16^{neg}/CD56^{bright}$ NK cell subset. Of course, greater fold differences of, for example, 2.5, 3.0, 3.5, 4.0, 4.5, 5.0, 5.5 or 6.0 further serve as reliable indicators for detection and diagnosis of ovarian cancer.

As an alternative to fold difference based on mean fluorescence intensity data, calculation of percentages of immune cells positive for sMUC16 and Siglec-9 may be used as indicators for detection and diagnosis of ovarian cancer. Various approaches may be adopted to obtain percentage-based indicator values. In one approach, a cocktail of fluorophore conjugated antibodies are used to define the NK, B, and monocyte subsets of immune cells isolated from the peripheral blood or peritoneal fluid of healthy volunteers and patients. The individual immune cell subsets are gated and the percentage of these gated cells that are positive for sMUC16 is determined by flow cytometry. In another approach, a cocktail of fluorophore conjugated antibodies are used to define the NK, B, and monocyte subsets of immune cells isolated from the peripheral blood or peritoneal fluid of healthy volunteers and patients. The individual immune cell subsets are gated and the percentage of these gated cells that are positive for Siglec-9 is determined by flow cytometry. In addition to flow cytometry, other methods such as negative selection, immunomagnetic bead separation, flow sorting, and cell enrichment media can be used to define percentage of immune cells that are positive for sMUC16 and/or Siglec-9.

The invention further encompasses kits containing reagents which facilitate methods according to the invention. Such kits include, for example: an anti-MUC16 antibody, labeled, if required; reagents to create a medium favorable to the immunological reaction between the anti-MUC16 antibody and MUC16 bound to immune cells within a biological sample or specimen; one or more reagents labeled, if required, capable of reacting with the anti-MUC16 antibody, or conjugates/immune complexes of the anti-MUC16 antibody and immune cell bound MUC16, to detect the conjugates/immunological complexes possibly formed; if applicable, a control and/or reference sample or biological medium. Exemplary reference samples may be peripheral blood samples of patients showing three levels of assay results, previously correlated to clinical outcome: low ovarian cancer risk; moderate ovarian cancer risk; and strong ovarian cancer risk. The kits may also include antibodies, labeled if required, against markers present on the immune cells to identify the types of cells that carry bound MUC16. The kits may further include instructional materials such as booklets and/or electronic media which describe use of the reagents, assay steps via, for example, flow cytometry, and/or interpretation of assay results.

In addition, kits for assay of MUC16 bound to immune cells may contain reagents for other assays so that the present MUC16-based methods may be practiced in combination with assays for other biomarkers, particularly gynecologic tumor markers, including, but not limited to, CA125 (i.e., cancer antigen 125), topoisomerase II, melan-A and inhibin-alpha, mesothelin, HE4, carbohydrate antigen 19-9, ferritin, beta chorionic gonadotropin (hCG), urinary gonadotropin fragment, carcinoembryonic antigen (CEA), alpha-fetoprotein (AFP), tumor-associated trypsin inhibitor, cyclin E, Lysophosphatidic acid, insulin-like growth factor-binding protein-3, OVX1, macrophage colony-stimulating factor, or combinations thereof.

In another aspect of the invention, yet another method to detect ovarian cancer in a subject is provided. Such a method includes steps of: (a) obtaining a sample of immune cells from a subject; and (b) measuring the sample of immune cells from the subject for Siglec-9 expressed on immune cells contained in the sample, wherein an elevated level of Siglec-9 bound to the immune cells indicates ovarian cancer in the subject.

In certain embodiments, an antibody specific for Siglec-9 is used to measure the level of Siglec-9 expressed on the immune cells and the level of Siglec-9 expressed on the immune cells is determined by flow cytometry detection of the antibody specific for Siglec-9. Detection of the immune complex comprising the antibody specific for Siglec-9 and Siglec-9 expressed on the immune cells may be carried out by radioisotopic, enzymatic, fluorogenic, chemiluminescent, or electrochemical means.

In certain embodiments, the method is repeated at least once with said subject in order to monitor the progress of ovarian cancer in the subject.

It is preferred that step (b) of measuring Siglec-9 expressed on the immune cells is based on immune cells selected from Siglec-9 expressing natural killer cells, B cells, monocytes, neutrophils, or mixtures thereof contained within the sample. In particular, step (b) preferably measures the expression of Siglec-9 on natural killer cell subsets $CD16^{pos}/CD56^{dim}$ and $CD16^{neg}/CD56^{bright}$ present in the immune cells contained within the sample in order to obtain a distribution of Siglec-9 between said subsets. An elevated level of Siglec-9 expressed on the $CD16^{neg}/CD56^{bright}$ subset as compared to the $CD16^{pos}/CD56^{dim}$ subset indicates ovarian cancer in the subject.

In another aspect, and in view of the results provided by the inventors in the Example section below, the invention is directed to a method to detect preeclampsia in a pregnant subject. Such a method includes steps of: (a) obtaining an immune cell sample from a pregnant subject; and (b) measuring expression of Siglec-9 on natural killer cell subsets $CD16^{pos}/CD56^{dim}$ and $CD16^{neg}/CD56^{bright}$ contained within the immune cell sample in order to obtain a distribution of Siglec-9 between the subsets, wherein a higher level of Siglec-9 on the $CD16^{neg}/CD56^{bright}$ subset as compared to the $CD16^{pos}/CD56^{dim}$ subset indicates preeclampsia in the pregnant subject. It is preferable that the level of Siglec-9 on the $CD16^{neg}/CD56^{bright}$ subset is at least 1.5 fold higher than the Siglec-9 on the $CD16^{pos}/CD56^{dim}$ subset to be indicative of the preeclampsic condition. Furthermore, the immune cell sample is preferably a peripheral blood sample.

Based on data from preeclamptic women and normal pregnant women (see, e.g., FIG. 17) the inventors have observed that between 1.5 to 3-fold higher levels of Siglec-9 are expressed on the $CD16^{neg}/CD56^{bright}$ NK cell subsets of preeclamptic women as compared to the normal pregnant females. Accordingly, at least a 1.5 fold higher level of Siglec-9 expressed on the $CD16^{neg}/CD56^{bright}$ NK cell subsets of preeclamptic women as compared to the normal pregnant females is indicative of the preeclampsic condition. Of course, greater fold differences of, for example, 2.0, 2.5 or 3.0 are further useful as indicators of a preeclamptic condition.

The invention further encompasses a method to detect preeclampsia in a pregnant subject which includes the steps of: (a) obtaining an immune cell sample from a pregnant subject; and (b) measuring binding of MUC16 to natural killer cell subsets $CD16^{pos}/CD56^{dim}$ and $CD16^{neg}/CD56^{bright}$ contained within the immune cell sample in order to obtain a distribution of MUC16 between said subsets, wherein a higher level of MUC16 bound to the $CD16^{neg}/CD56^{bright}$ subset as compared to the $CD16^{pos}/CD56^{dim}$ subset indicates preeclampsia in the pregnant subject. It is preferable that the level of MUC16 bound to the $CD16^{neg}/CD56^{bright}$ subset is at least 2 fold higher than the MUC16 bound to the $CD16^{pos}/CD56^{dim}$ subset. Also, the immune cell sample is preferably a peripheral blood sample.

Based on data from preeclamptic patients (see, e.g., FIG. 16) it is found that approximately 2-4 fold higher levels of sMUC16 are present on the $CD16^{neg}/CD56^{bright}$ NK cell subsets as compared to the $CD16^{pos}/CD56^{dim}$ NK cells. The elevated levels of sMUC16 on the $CD16^{neg}/CD56^{bright}$ NK cell subsets serve as markers for preeclampsia. Accordingly, at least a 2 fold higher level of sMUC16 present on the $CD16^{neg}/CD56^{bright}$ NK cell subset as compared to the $CD16^{pos}/CD56^{dim}$ NK cell subset is indicative of the preeclampsic condition. Of course, greater fold differences of 2.5, 3.0, 3.5 or 4.0 are further useful as indicators of a preeclamptic condition.

The invention will be more fully understood upon consideration of the following non-limiting Examples.

EXAMPLES

Example 1

Materials and Methods

This example describes the general materials and methods utilized by the inventors to generate the results set forth in subsequent examples below.

Sample Processing. The peripheral blood ("PB") and peritoneal fluid ("PF") samples were obtained from epithelial ovarian carcinoma ("EOC") patients (designated PT#24, PT#36, etc) recruited at the time of their initial diagnosis. None of the EOC patients had been previously treated for this disease at the time of PB and PF sample collection. All patients, pregnant women (designated HP#1, HP#2, etc) and healthy donors (designated HD#1, HD#2, etc) signed an informed consent and the studies were approved by the Institutional Review Board of University of Wisconsin-Madison. The PB and PF samples were collected and processed as described previously (Belisle, J. A., Gubbels, J. A., Raphael, C. A., Migneault, M., Rancourt, C., Connor, J. P., and Patankar, M. S. Peritoneal natural killer cells from epithelial ovarian cancer patients show an altered phenotype and bind to the tumour marker MUC16 (CA125). Immunology, 2007).

Flow Cytometry. Cryopreserved or freshly obtained mononuclear cells from the PB or PF samples were analyzed. The cells were processed and labeled with antibodies as described previously (Belisle, et al., Immunology, 2007). For blocking purposes, cells were first incubated for 15 minutes with goat antibody before staining with the anti-MUC16 antibody VK8, or the anti-galectin-1 antibody, LGALS-1 (Abnova, Taipei, Taiwan). After washing, FITC or APC-conjugated goat anti-mouse (GAM) secondary antibody was added to the cells at 1:100 or 1:150 dilution, respectively. Following washing, the cells were incubated with mouse IgG for 15 minutes to bind any additional Fab sites on the GAM secondary. The cells were then incubated with various cocktails of directly conjugated antibodies to stain for CD3 (APC-Cy7), CD45 (PerCP-Cy5.5), CD33 (PerCP-Cy5.5), CD56 (Alexa® 700), CD16 (PE-Cy7), NKp46 (APC), CD19 (PE), CD158a (PE), CD158b (PE), CD158e (PE), CD226 (PE), CD244 (PE), NKG2A (PE), NKG2D (PE), NKp44 (PE), or Siglec-9 (FITC). After a final wash, cells were resuspended in ~300 uL of phosphate buffered saline containing 1% bovine serum albumin (PBS-BSA). Immediately before data acquisition on an LSRII (Beckton Dickinson) flow cytometer, the viability indicator DAPI (1:300; BD Biosciences) was added to each sample. Because of the complexity of compensation with multi-color flow cytometry, automatic computerized compensation was utilized to create the compensation matrix. To compare the values of samples acquired on different days, SPHERO™ Rainbow Fluorescent Particles (BD Biosciences) were used to set instrument voltages.

To determine if treatment with fetuin could result in elution of sMUC16 from the surface of the NK cells, mononuclear cells from the PB of ovarian cancer patients were washed with PBS-BSA. The cells were incubated with 1 mg/ml of fetuin or asialofetuin. Control cells were incubated in media only. Following 1.5 h incubation at 4° C., the cells were washed with PBS-BAS and stained for sMUC16 (VK-8) and CD3, CD16, CD45, and CD56 using the protocol described above. The cells were then analyzed for sMUC16 binding by flow cytometry.

FlowJo software (v. 4.6.1, TreeStar) was used for analysis of the raw flow cytometry data, and comparison of the data was done using GraphPad Prism software (v. 4, GraphPad Software, Inc.). For statistical significance, GraphPad Prism was used to analyze samples using a nonparametric Wilcoxon Signed Rank test or a student t-test with two-sided p-values, where $p<0.05$ indicated significance.

Western and Far-Western Blotting. The sMUC16 (isolated from culture media of OVCAR-3 cells as described earlier (Kui Wong, N., Easton, R. L., Panico, M., Sutton-Smith, M., Morrison, J. C., Lattanzio, F. A., Morris, H. R., Clark, G. F., Dell, A., and Patankar, M. S. Characterization of the oligosaccharides associated with the human ovarian tumor marker CA 125. J Biol Chem, 278: 28619-28634, 2003) and fetuin were separated on a 4% stacking/7.5% resolving gel. The separated proteins were blotted on to a PVDF membrane. After blocking with BSA, the membranes were overlaid with either the VK-8 antibody or with Siglec-9-human Fc chimera (R&D Systems). To detect the binding of the VK-8 antibody or of the Siglec-9-human Fc chimera, the membranes were overlaid with horseradish peroxidase conjugated goat anti-mouse or a goat anti-human Fc secondary antibodies, respectively. The blots were developed using chemiluminescence substrates (Pierce).

For inhibition of Siglec-9 binding to sMUC16 by fetuin or asialofetuin, the Siglec-9-human Fc was pre-incubated for 5 min with 3-fold molar excess of fetuin or asialofetuin. The Siglec-9-human-Fc along with the fetuin or asialofetuin was overlaid on membranes blotted with sMUC16. After incubation for 60 mins, the binding of the Siglec-9-human Fc chimera to the blots was detected as described above.

Neuraminidase treatment of MUC16 and PBMC. sMUC16 (2000 U of CA125) isolated from the spent media of OVCAR-3 was treated with 1U of neuraminidase from *Clostridium perfringens* (Sigma Aldrich) in 100 mM sodium acetate buffer (pH 5.5) in a total of 100 uL for 16 h at 37° C. A control sample of MUC16 containing 2000U CA125 was subjected to the same treatment without the addition of neuraminidase.

For treatment of cells, PB mononuclear cells were thawed, washed 2 times in PBS-BSA, and resuspended at $5 \times 10^5$ cells/mL in RPMI containing 0.05M HEPES. The cells were incubated with neuraminidase dissolved in RPMI containing 0.05M HEPES at 100 mU/mL for 15 minutes at room temperature before being washed twice in PBS-BSA and stained for flow cytometry. Control cells were treated under identical conditions except that neuraminidase was not added.

Binding of sMUC16 to Siglec expressing Jurkat cells. The Siglec-7pos and Siglec-9pos Jurkat cells were washed in culture media (RPMI 1640 containing 10% fetal calf serum, non-essential amino acids and G418) and incubated for 0, 24, and 48 h in media containing sMUC16 (25,000 U CA125/ml) isolated from OVCAR-3 cells, or in a mixture of 90% PF, and 10% fetal calf serum containing non-essential amino acids and G418. Following incubation the cells were washed twice and stained for flow cytometry as described above.

Example 2 sMUC16 is present on NK Cells Even when Serum CA125 is Undetectable

This example describes the inventors determination that sMUC16 is present on the surface of NK cells from the PB and PF of ovarian cancer patients. This mucin is also expressed in the endometrium during the mid-secretory phase of the menstrual cycle. Elevated levels of sMUC16 (detected as CA125) are also detected in the sera of pregnant women. The inventors have previously shown that NK cells from the PB of pregnant women also carry sMUC16 on their surface. The inventors have now extended this initial observation and show that sMUC16 can be detected on the NK cells of women in the 9$^{th}$ and 18$^{th}$ week of pregnancy (FIG. 1). Furthermore, the percentage of NK cells positive for sMUC16 or the amount of sMUC16 present on the cells (detected by measuring mean fluorescence intensity, MFI) could not be completely correlated with the amount of CA125 detected in the sera (FIG. 1). More importantly, even when the serum CA125 levels were relatively low or undetectable, significant amounts of sMUC16 could be detected on the NK cells by flow cytometry (FIG. 1).

Example 3

Potential sMUC16 Receptors on the NK Cell Surface

This example demonstrates that the detection of sMUC16 on the NK cells even at low serum CA 125 levels may provide an alternate means of monitoring ovarian tumor progression. The successful implementation of a useful test requires clear identification of the receptors for sMUC16 on the NK cell surface. Galectin-1 has already been shown to be a receptor for MUC16 and is known to be expressed on NK cells. Flow cytometry experiments on NK cells from the PB and PF of epithelial ovarian cancer patients indicated that galectin-1 was mainly expressed on the CD16$^{neg}$/CD56$^{br}$ NK cells (FIG. 2). Since sMUC16 primarily binds to the CD16$^{pos}$/CD56$^{dim}$ NK cell subset galectin-1 was ruled out as the receptor for this mucin.

Another binding partner for sMUC16 is mesothelin. This glycoprotein is however not expressed on the NK cells based on microarray analysis reported previously. The inventors therefore investigated other potential NK cell receptors as binding partners for sMUC16. A thorough survey of the literature indicated that Siglec-9, an I-type lectin receptor, was expressed on a subset of NK cells. Siglec-9 also bears the Immuno receptor Tyrosine-based Inhibitory Motif (ITIM) and is known to inhibit immune cell responses. MUC16 also was a potent suppressor of NK cell responses and expresses 2-3-linked sialic acids which are preferentially recognized by Siglec-9. The inventors therefore performed experiments to determine if MUC16 binds to the NK cells via Siglec-9.

The inventors subsequently determined that sMUC16 binds to Siglec-9. In far western blot analysis sMUC16 purified from OVCAR-3 cells was detected by the Siglec-9-human Fc chimera (FIG. 3A). Fetuin, a sialylated glycoprotein from bovine serum blocked the binding of Siglec-9 human Fc chimera to sMUC16 (FIG. 3B). Co-incubation with asialofetuin under identical conditions did not inhibit the binding of Siglec-9-human Fc to sMUC16.

To further demonstrate that Siglec-9-human Fc was recognizing the sialic acids of sMUC16 the mucin was digested with neuraminidase. Efficient desialylation of sMUC16 was demonstrated by the faster migrating asialo-sMUC16 band detected by western blot analysis using the anti-MUC16 antibody VK-8 (FIG. 3C). The desialylated sMUC16 was not recognized by the Siglec-9-human Fc chimera (FIG. 3C).

Specificity of sMUC16 binding to Siglec-9 was also determined using Jurkat cells transfected with this I-type lectin. The Siglec-9 expressing Jurkat cells were incubated with either the sMUC16 (50,000 U of CA125/ml) purified from the spent media of OVCAR-3 cells or with PF from two ovarian cancer patients. After culture for 24 h (FIG. 3D) or 48 h (data not shown) sMUC16 was detected on the Siglec-9 expressing Jurkat cells. Matched Jurkat cells that expressed Siglec-7 and not Siglec-9, did not show any binding of sMUC16 under identical conditions (FIG. 3D). Siglec-7 is an I-type lectin that preferentially binds to 2-8-linked sialic acids that are not expressed on sMUC16 (8, 20).

Example 4 sMUC16 Binds to Siglec-9 Expressing NK Cells

This example describes the inventors determination that sMUC16 binds to Siglec-9 expressing NK cells. Previous reports suggested that Siglec-9 was expressed only on a subset of human NK cells. Multi-color flow cytometry experiments on NK cells derived from three healthy donors indicated that Siglec-9 was expressed only on approximately 15-30% of the CD16$^+$/CD56$^{dim}$ cells. The CD16$^-$/CD56$^{br}$ NK cells were either negative or expressed very low levels of Siglec-9 (FIG. 4A). A similar expression pattern for Siglec-9 was also observed on the NK cells from the PB and PF of epithelial ovarian cancer patients (FIG. 4A).

Analysis of the NK cells from the PB and PF of epithelial ovarian cancer patients indicated that greater than 90% of the cells that were expressing Siglec-9 were also positive for sMUC16 (FIG. 4B). Likewise, all of the sMUC16$^{pos}$ NK cells also expressed Siglec-9 (FIG. 4B). Fetuin was able to block the binding of Siglec-9-human Fc to sMUC16 in western blot assays (FIG. 3B). However, incubation of the NK cells from the PB and PF of epithelial ovarian cancer patients with fetuin did not result in elution of sMUC16 from the cell surface (FIG. 4C). Digestion of the immune cells derived from the PF of epithelial ovarian cancer patients with neuraminidase led to a significant decrease in the amount of NK cell bound sMUC16 (FIG. 4D).

Example 5 sMUC16 also Binds to Siglec-9 Expressing B Cells and Monocytes

This example describes the inventors determination that sMUC16 also binds to Siglec-9 expressing B cells and monocytes. In addition to the NK cells, Siglec-9 is also expressed on approximately 30% of the CD19$^{pos}$ B cells and on >90% of the CD33$^{pos}$ monocytes of healthy individuals (FIG. 5A). Similar distribution of Siglec-9 was also observed on the B cells and monocytes isolated from the PB and PF of epithelial ovarian cancer patients (FIG. 5A). sMUC16 was detected on the Siglec-9$^{pos}$ B cells and monocytes from the PB and PF of these patients (FIG. 5A,B). Similar to the NK cells, sMUC16 was present primarily on the B cells and monocytes that expressed Siglec-9 and vice versa (FIG. 5B).

Example 6

Turnover of sMUC16 from Immune Cell Surface

This example describes the inventors' determination that turnover of sMUC16 from immune cell surfaces is relatively slow. The cytotoxicity of sMUC16 treated NK cells continues to be inhibited 24 h after the removal of sMUC16 from the culture media. The differential expression pattern of Siglec-9 on the NK cells, B cells and the monocytes suggested that some of these immune cell subsets may retain sMUC16 on their surface for longer periods than others. This property would be an important parameter in devising a diagnostic test for monitoring ovarian cancer progression. The inventors therefore studied the turnover of sMUC16 from the surface of the NK cells, B cells, and monocytes derived from the PB of ovarian cancer patients after these cells had been cultured in media for 24 and 48 h. A temporal decrease in sMUC16 from the surface of the immune cells was observed in these experiments (FIG. 6A). However, the decrease in the sMUC16 was most pronounced on the NK cells and B cells while the monocytes continued to display significant amounts of sMUC16 on their surface even after 48 h incubation in the culture media (FIG. 5A). The slower loss of sMUC16 from the monocyte surface is likely due to the increased expression of Siglec-9 and the elevated levels of sMUC16 on these cells as compared to the NK cells and the B cells (FIG. 5A).

The inventors further determined that sMUC16 bound immune cells do not show any decrease in their viability. Cross-linking of Siglec-9 on the neutrophils by specific antibodies results in their autophagic cell death. However, neither the NK cells, the B cells nor the monocytes from the PB or PF of ovarian cancer patients, that were sMUC16$^{pos}$, showed increased cell death (FIG. 6B).

Example 7

MUC16 and Siglec-9 as Biomarkers for Ovarian Cancer and Preeclampsia

This example further demonstrates (1) the immunoregulatory role of MUC16, (2) the binding of MUC16 to immune cells of ovarian cancer patients, (3) identification of Siglec-9 as the MUC16 receptor, and (4) binding of MUC16 to different subsets of NK cells in normal pregnancy and in preeclampsia. The immunomodulatory role of MUC16 is described here to only highlight the specific biological effects of MUC16 on the immune cells. The data presented here further demonstrates our ability to process and cryopreserve blood derived immune cells and to conduct the subsequent flow cytometry procedures.

NK Cell Phenotype.

Figure 7:
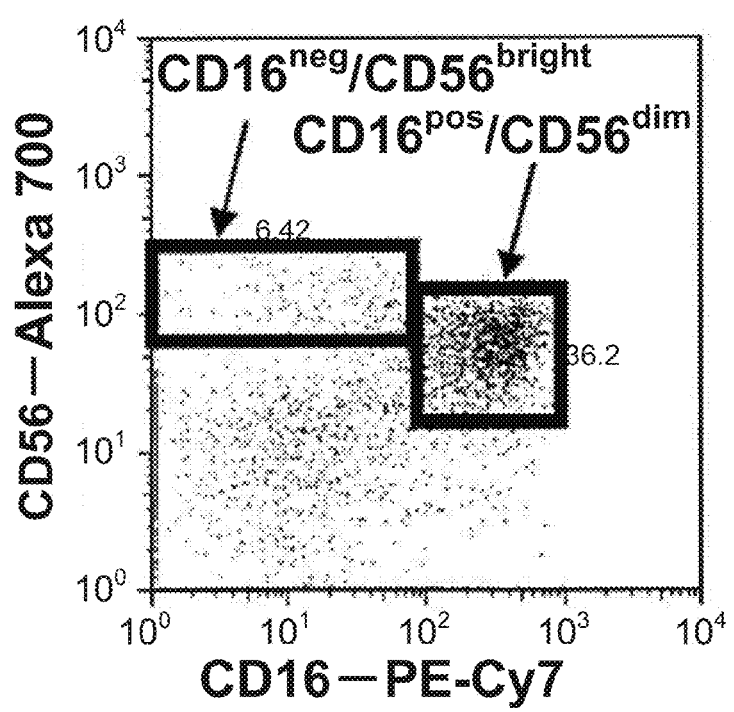
FIG. 7. Classification of NK cell subsets based on expression of CD16 and CD56.
Figure 8:
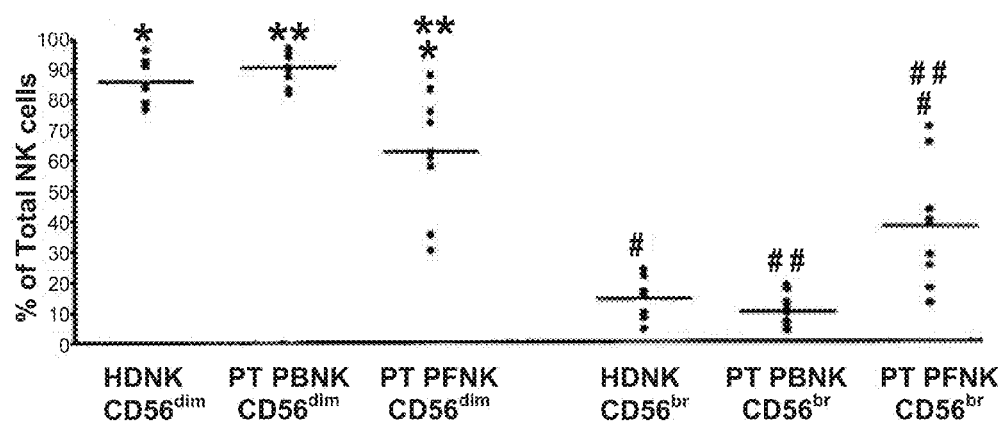
FIG. 8. Relative distribution of CD16$^{pos}$/CD56$^{dim}$ and CD16$^{neg}$/CD56$^{bright}$ NK cells in peripheral blood (PB) of seven healthy donors (HD) and PB and peritoneal fluid (PF) of nine ovarian cancer patients (PT). *, **, #, ##p<0.01.

NK cells are categorized into tow subtypes based on the expression levels of CD16 (an Fc receptor) and CD56 (NCAM). Greater than 90% of all NK cells in the peripheral blood of healthy individuals are of the CD16$^{pos}$/CD56$^{dim}$ phenotype and the remaining NK cells are CD16$^{neg}$/CD56$^{bright}$ (FIG. 7). Identical phenotypic distribution is observed for NK cells from peripheral blood of ovarian cancer patients (FIG. 8). Peritoneal NK cells from ovarian cancer patients have a significantly different phenotype, however (FIG. 8).

MUC16 Inhibits Cytoytic Responses of NK Cells.

Figure 9:
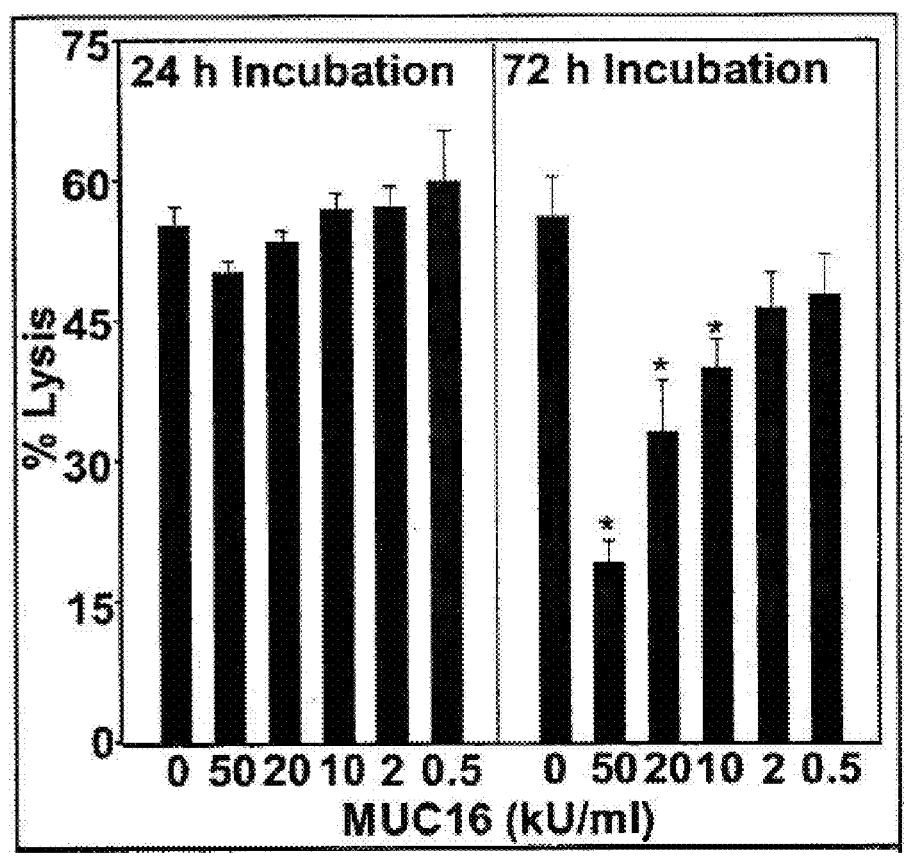
FIG. 9. Prolonged incubation with MUC16 inhibits NK cell cytotoxicity. NK cells from healthy donors were incubated with MUC16 for 24 or 72 h. After incubation the ability of NK cells to lyse K562 target cells was measured. Data is representative of five separate experiments performed on NK cells from 5 donors. *P values<0.01.

We tested the effect of MUC16 on ability of NK cells to lyse $^{51}$Cr labeled K562 cells). A dramatic reduction in K562 cell lysis was observed when the NK cells were pre-treated with MUC16 for 72 h exposure to MUC16 did not decrease proliferation or induce apoptosis of the NK cells. This data is illustrated in FIG. 9 and is presented to highlight the biological effect of MUC16 on immune cells.

MUC16 Binds to the Surface of NK Cells.

During our analysis of NK cells from ovarian cancer patients, we observed that MUC16 could be detected on the surface of healthy donor NK cells that were incubated in vitro with physiologic concentrations of this mucin. Exhaustive analysis of peripheral blood and peritoneal NK cells from 20 ovarian cancer patients has indicated that approximately 30-40% of the CD16$^{pos}$/CD56$^{dim}$ NK cells were positive for MUC16 (FIG. 10A,B). Invariably, very low levels of MUC16 were detected on the CD16$^{neg}$/CD56$^{bright}$ NK cells isolated from the peripheral blood of ovarian cancer patients (FIG. 10B). NK cells from peripheral blood of healthy donors were never positive for MUC16 (FIG. 10A). Only in one case we observed MUC16 on NK cells of a non-cancer control. However, it was later found that this female blood donor was diagnosed for endometriosis, a condition where serum CA125 (MUC16) levels are elevated.

RT-PCR experiments indicated that NK cells were not expressing endogenous MUC16 (FIG. 10C). Instead the NK cells were binding to MUC16 present in the serum or the peritoneal fluid of ovarian cancer patients. This was clearly demonstrated by incubating immune cells from healthy donors with peritoneal fluid from ovarian cancer patients. These in vitro cultured healthy donor immune cells became positive for MUC16 (FIG. 11).

MUC16 Specifically Binds to NK Cells Via Siglec-9.

Figure 12:
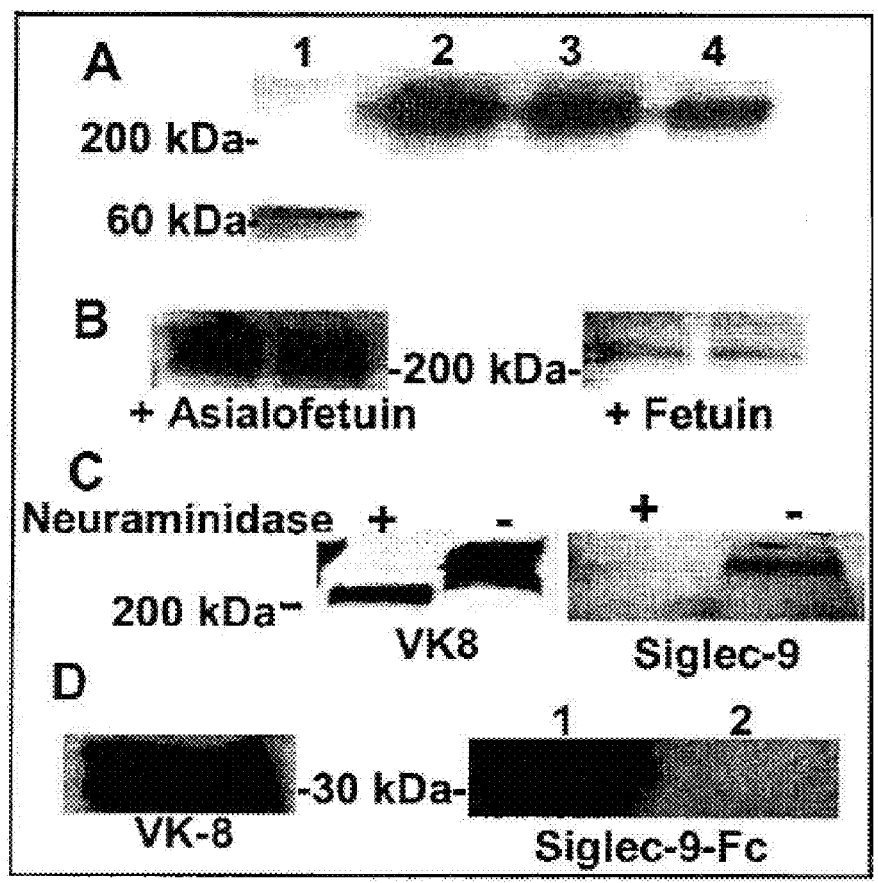
FIG. 12. Siglec-9 bind to sialylated MUC16 glycans. A) Binding of Siglec-9-human Fc chimera to electroblotted fetuin (lane 1) or MUC16 (300 U of CA125, lane 2; 200 U of CA125, lane 3; and 100 U if CA125, lane 4) was detected using HRP-conjugated secondary. B) Binding of Siglec-9-human Fc chimera to MUC16 (205 U of CA125/lane loaded in duplicate/blot) is blocked by 3-fold molar excess of detuin (right panel). C) Desialyation of MUC16 increases its mobility (detected by VK-8, left panel) and abrogates binding by Siglec-9-human Fc chimera (right panel). D) Recombinant MUC16 fragment containing one tandem repeat of the mucin, MUC16-1R, is recognized by anti-MUC16 antibody VK-8 and also binds to Siglec-9-Fc (lane 1). PNGaseF treated MUC16-1R (lane 2) does not bind to Siglec-9-Fc.

The fact that MUC16 was only present on 30-40% of CD16$^{pos}$/CD56$^{dim}$ NK cells suggested that the mucin was likely not binding to NK cells in a non-specific manner. We therefore investigated the possibility that MUC16 was being recognized by a specific NK cell receptor. Various preliminary experiments led us to demonstrate that the receptor for MUC16 was the I-type lectin Siglec-9. Western blots using Siglec-9-Fc chimera showed that this receptor recognized MUC16 via terminal sialic acid residues present on the oligosaccharide chains of this mucin (FIG. 12). It was demonstrated that Jurkat cells transfected with Siglec-9 also became positive when incubated with purified MUC16 or peritoneal fluid of ovarian cancer patients (FIG. 13)

Figure 13:
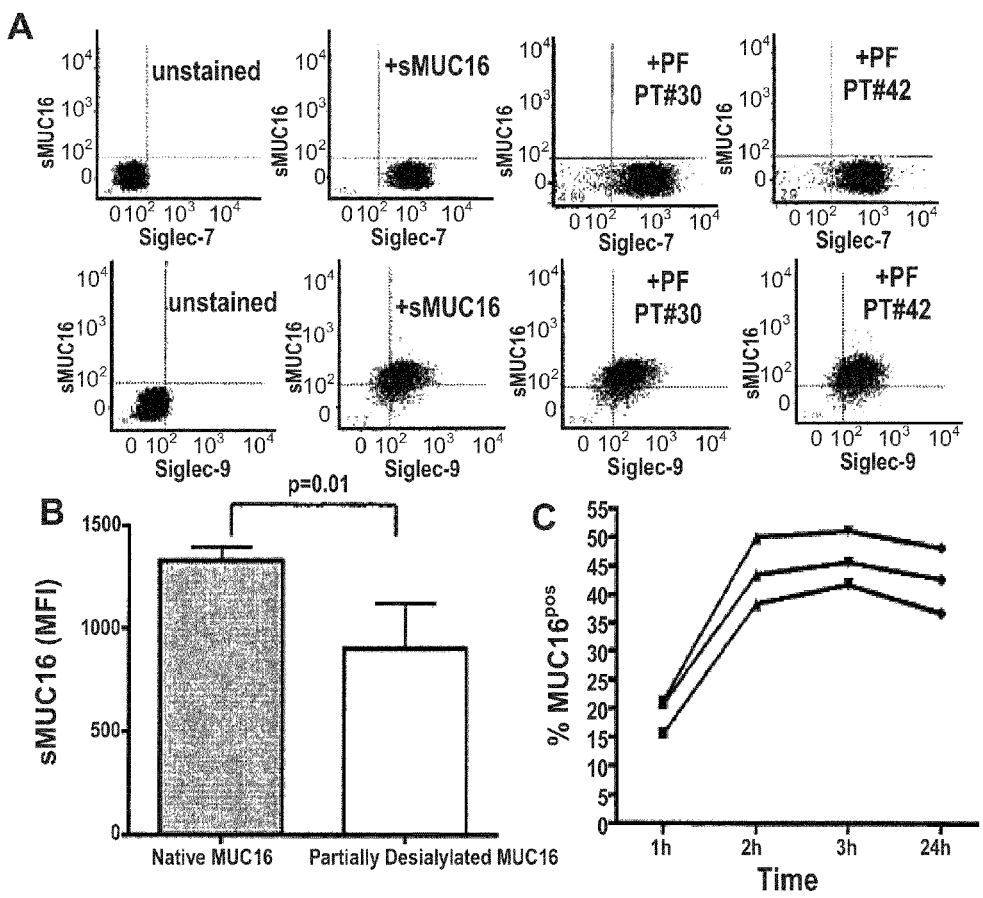
FIG. 13. MUC16 binds to Siglec-9 expressed on immune cells. A) Siglec-7 (top panel) and Siglec-9 (bottom panel) expressing Jurkat cells were incubated for 24 h in media, media containing purified MUC16 (50,000 U of CA125/ml), or in 10% media containing 90% peritoneal fluid from ovarian cancer patients (PT #30 and PT #42). VK-8 antibody was used to detect binding of MUC16 to cells by flow cytometry. B) Siglec-9 expressing Jurkat cells were incubated with native and partially desialylated MUC16 (50,000 U of CA125/ml) for 3 h. Cells were labeled with VK8 and the amount of MUC16 or partially desialylated MUC16 present of the surface was determined by flow cytometry. Mean and standard deviation of three separate experiments is shown. C) Siglec-9 expressing Jurkat cells were incubated for the designated time intervals with MUC16 (50,000 U of CA 125/ml). Cells were washed, labeled with VK-8 and an appropriate flurophore conjugated secondary. The amount of MUC16 on the cell surface was determined by flow cytometry. Each curve represents data from a single independent experiment.

On the other hand, Jurkat cells expressing Siglec-7 were unable to bind MuC16 under identical experimental conditions (FIG. 13). Siglec-7 is also a member of the I-type lectin family but preferably bind to α2-8-linked sialic acid residues that are not expressed on MUC16.

MUC16 is Present on all Siglec-9$^{pos}$ Immune Cells.

Figure 14:
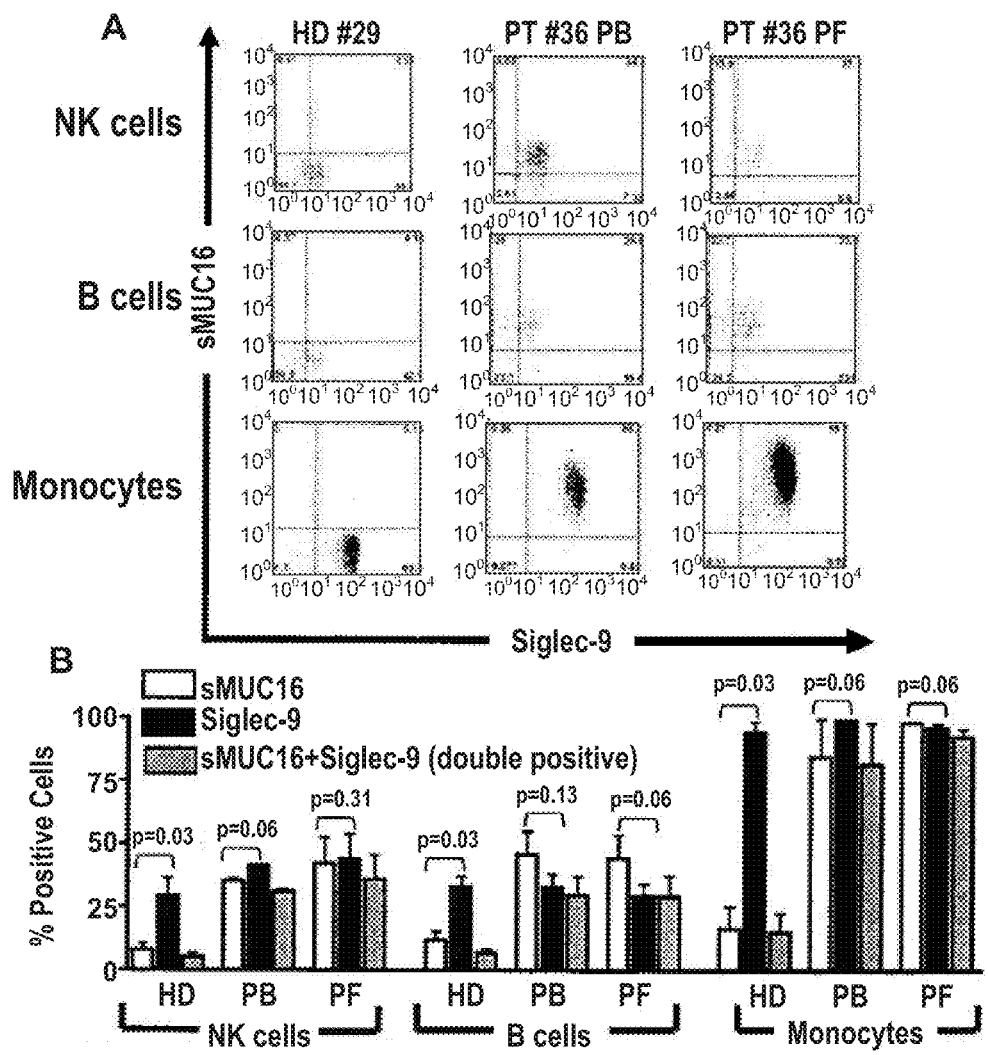
FIG. 14. MUC16 binds to Siglec-9$^{pos}$ NK cells, B cells, and monocytes. A) Mononuclear cells from the peripheral blood (PB) and peritoneal fluid (PF) of ovarian cancer patients and from the peripheral blood of healthy donors was tested by flow cytometry for MUC16 and Siglec-9. The percentage of cells positive for MUC16 and Siglec-9 was determined. Representative data is shown for cells from one ovarian cancer patient (PT#36) and one healthy donor (HD#29). B) Cumulative data on MUC16 binding and Siglec-9 expression on NK cells, B cells, and monocytes of nine patients and five healthy donors is shown.

Siglec-9 is expressed by approximately 20% of B cells and >90% of monocytes. Neutrophils are also positive for this receptor. We have now observed that in ovarian cancer patients, MUC16 is detected on the surface of all of the Siglec-9$^{pos}$ B cells and monocytes in addition to NK cells (FIG. 14). We anticipate that neutrophils from cancer patients will also be positive for MUC16.

MUC16 is Retained on Immune Cell Surface for Extended Periods.

Figure 15:
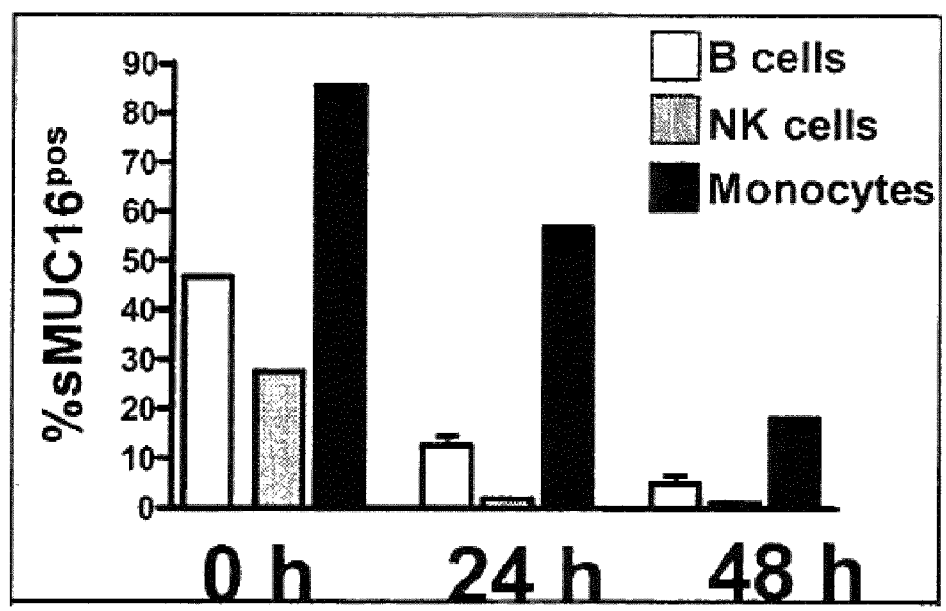
FIG. 15. MUC16 is retained on immune cell surface. Mononuclear cells from peripheral blood of ovarian cancer patients were cultured in media containing MUC16. Binding of MUC16 to individual immune subsets after designated time of culture was monitored by flow cytometry.

Immune cells from peripheral blood of ovarian cancer patients even when cultured in vitro in media not containing any MUC16 retain the mucin on their surface (FIG. 15). Siglec-9 is an endocytic receptor. However, we have hypothesized that because of its extensive molecular size, MUC16 once bound to Siglec-9 locks this receptor in the cell membrane and prevents it endocytosis. As a result, the mucin can be detected on the immune cell surface for extended periods of time.

Immune Cell Bound MUC16 is Detected Even when Serum CA125 Levels are Low.

Serum CA125 (MUC16) levels are elevated in pregnant women. Siglec-9 expressing immune cells from peripheral blood of pregnant women are positive for MUC16. The serum CA125 levels are maximum in the first trimester of pregnancy but decrease in the second and third trimester. The immune cell bound MUC16 however continues to be present at high levels even the second trimester. This can be explained by the fact that MUC16 in serum likely reduced in second trimester and hepatic uptake of the mucin causes reduction in free CA 125 levels in serum (FIG. 1). However, immune cell bound MUC16 is trapped on the cell surface and is not available for rapid hepatic degradation. Blood samples from only three pregnant women were analyzed in this limited time study and MUC16 binding to $CD16^{pos}/CD56^{dim}$ and $CD16^{neg}/CD56^{bright}$ NK cells was not determined at the time.

Differential MUC16 binding pattern in peripheral blood NK cells during pregnancy. MUC16 is expressed by the human decidua. We isolated decidual NK cells from placental samples obtain at term from normal pregnant women. MUC16 was detected on the surface of $CD16^{pos}/CD56^{dim}$ and the $CD16^{neg}/CD56^{bright}$ decidual NK cells (data not shown). Even more interesting results were obtained when NK cells from the peripheral blood drawn at term from normal pregnant women and patients with preeclampsia were analyzed by cytometry.

Ten normal pregnant women were consented for this study along with five women with preeclampsia. In both normal pregnant and preeclamptic women approximately 90% of the peripheral blood NK cells were of the $CD16^{pos}/CD56^{dim}$ phenotype and the remaining were $CD16^{neg}/CD56^{bright}$. In contrast to NK cells from healthy donors and ovarian cancer patients equal levels of Siglec-9 were determined on the $CD16^{pos}/CD56^{dim}$ and the $CD16^{neg}/CD56^{bright}$ subsets of NK cells isolated from the peripheral blood of normal pregnant women (FIG. 16).

Figure 16:
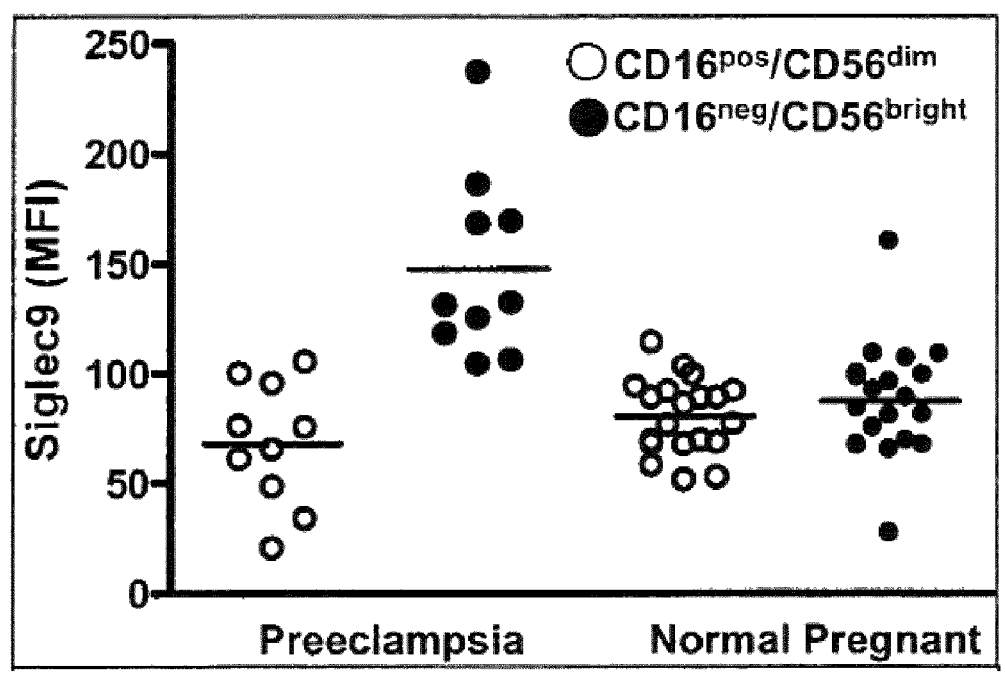
FIG. 16. Distribution of Siglec-9 on NK cell subsets from peripheral blood of normal pregnant and preeclamptic women. Duplicate flow cytometry measurements from five preeclamptic and 10 normal pregnant women are shown. Related statistics are provided in Table 1.
Figure 17:
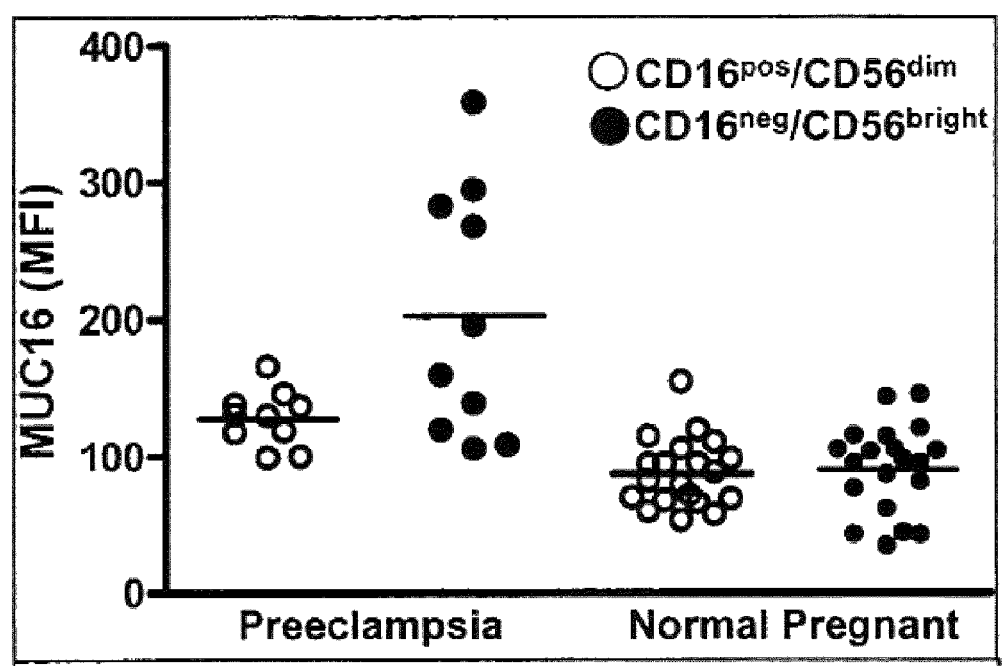
FIG. 17. Binding of MUC16 to NK cells subsets from peripheral blood of normal pregnant and preeclamptic women. Duplicate flow cytometry measurements from five preeclamptic and 10 normal pregnant women are shown. Related statistics are provided in Table 1.

On the other hand, higher levels of Siglec-9 were expressed on $CD16^{neg}/CD56^{bright}$ NK cells from peripheral blood of preeclamptic women as compared to their $CD16^{pos}/CD56^{dim}$ NK cells (FIG. 16). MUC16 binding to these subsets closely match the Siglec-9 expression on peripheral blood NK cells from both normal pregnant women and patients with preeclampsia. The MUC16 binding pattern to NK cell subsets during pregnancy is in sharp contrast to that observed in ovarian cancer patients (FIG. 17 versus FIG. 10B). Results from FIGS. 16 and 17 suggest that in addition to immune cell bound MUC16, even the expression levels of Siglec-9 could potentially be used as biomarker for ovarian cancer and preeclampsia. Statistical analysis for FIGS. 16 and 17 is in Table 1.

Figure 10:
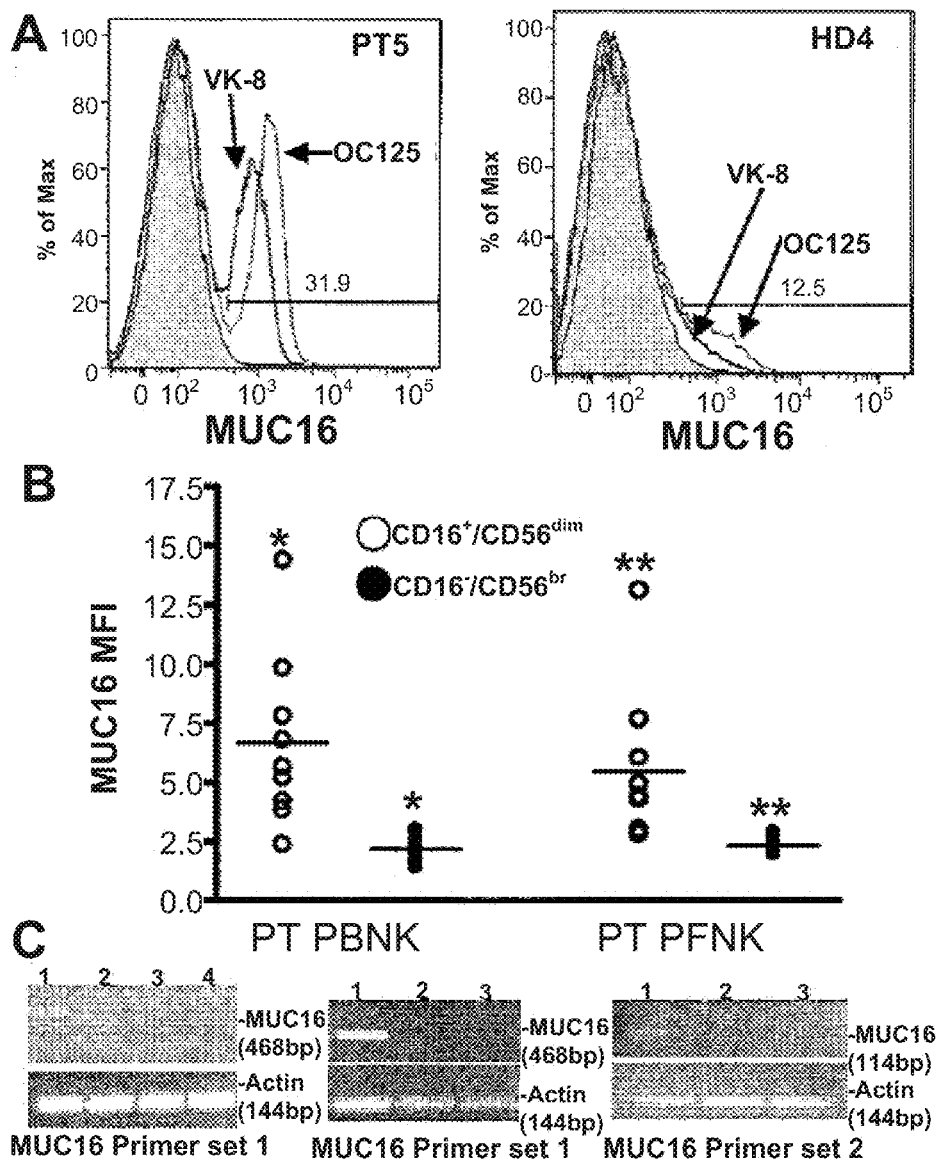
FIG. 10. MUC16 binds to PBMC of ovarian cancer patients. A) Anti-MUC16 antibodies VK-8 and OC125 bind to PBMC from ovarian cancer patient #5 (left panel) but not to PBMC from healthy donor #4 (right panel). Similar results were obtained on 15 cancer patients and 10 healthy donor PCMB samples. B) Mean Fluorescence Intensity (MFI) data from nine ovarian cancer patients showing MUC16 is preferentially present on CD16$^{pos}$/CD56$^{dim}$ NK isolated from peripheral blood (PBNK) and peritoneal fluid (PFNK). C) MUC16 mRNA is not detected in PBMC from three HD (left panel, lanes 2-4) or four ovarian cancer patients (PT) (middle and right panels, lanes 2 and 3). Lane 1 in all panels is OVCAR-3 positive control.
Figure 11:
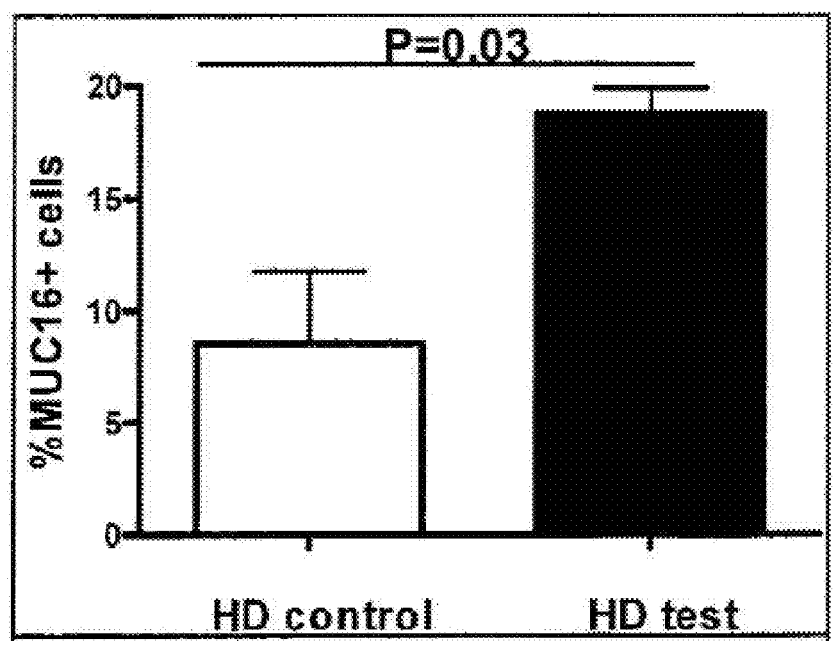
FIG. 11. MUC16 from peritoneal fluid of ovarian cancer patients binds to healthy donor immune cells. PBMC from three healthy donors (HD) were incubated separately with peritoneal fluid (test) or with media only (control). After 72 h culture MUC16 on the cells was determined by flow cytometry and average data for all three PCMC samples was plotted.

It must be noted that in all of the experiments shown in FIGS. 10 and 17 the VK8 antibody at the same concentration (1:100 titer) and from the same lot was used as the MUC16 detection reagent. Binding of VK8 to the immune cells was detected by using a goat anti mouse secondary. In experiments conducted with NK cells from ovarian cancer patients (FIG. 10), a FITC conjugated secondary was used whereas an APC labeled secondary was used in assays with NK cells from normal pregnant and preeclamptic women (FIG. 17). The use of different flourophores is the reason for the differences in the scales for mean fluorescent intensities (MFI) shown in FIGS. 10B and 17. The change in the detecting antibodies was made to accommodate the remaining 6-7 fluorophore conjugated antibodies used to detect surface antigens on immune cells from pregnant women in this multi-color flow cytometry assay. Because of the change in the secondary antibodies we are unable to directly compare the level of MUC16 binding to immune cells from ovarian cancer patients versus those from normal pregnant preeclamptic women. However, comparing the pattern of binding of MUC16 to $CD16^{pos}/CD56^{dim}$ and $CD16^{neg}/CD56^{bright}$ NK cells within each of these three cohorts is still possible. Furthermore, the trends in MUC16 binding to the two NK cell subsets match the expression of Siglec-9 on these subsets in pregnant women, preeclampsia and ovarian cancer. In all cases Siglec-9 was detected using the same fluorophore conjugated anti-human Siglec-9 antibody.

TABLE 1

Mann-Whitney statistics of data from FIGS. 16 & 17

|  |  | Dim PE | Bright PE | Dim NP | Bright NP |
| --- | --- | --- | --- | --- | --- |
| Siglec-9 (FIG. 13) | Dim PE | — | $P < 0.0001$ | $P = 0.3$ | $P = 0.08$ |
|  | Bright PE | $P < 0.0001$ | — | $P < 0.0001$ | $P = 0.0001$ |
|  | Dim NP | $P = 0.3$ | $P < 0.0001$ | — | $P = 0.32$ |
|  | Bright NP | $P = 0.08$ | $P < 0.0001$ | $P = 0.32$ | — |
| MUC16 (FIG. 14) | Dim PE | — | $P = 0.06$ | $P = 0.0004$ | $P = 0.0032$ |
|  | Bright PE | $P = 0.06$ | — | $P < 0.0001$ | $P = 0.0002$ |
|  | Dim NP | $P = 0.0004$ | $P < 0.0001$ | — | $P = 0.49$ |
|  | Bright NP | $P = 0.0032$ | $P = 0.0002$ | $P = 0.49$ | — |

Dim—$CD16^{pos}/CD56^{dim}$; Bright $CD16^{neg}/CD56^{bright}$; PE—Preeclampsia; NP—Normal Pregnant.

Those skilled in the art will recognize, or be able to ascertain using no more than routine experimentation, numerous equivalents to the specific methods, assays and reagents described herein. Such equivalents are considered to be within the scope of this invention and encompassed by the following claims.

What is claimed is:

1. A method to detect preeclampsia in a pregnant subject, comprising:
   (a) obtaining an immune cell sample from a pregnant subject; and
   (b) measuring expression of Siglec-9 on natural killer cell subsets $CD16^{pos}/CD56^{dim}$ and $CD16^{neg}/CD56^{bright}$ contained within the immune cell sample in order to obtain a distribution of Siglec-9 between said subsets, wherein a higher level of Siglec-9 on the $CD16^{neg}/CD56^{bright}$ subset as compared to the $CD16^{pos}/CD56^{dim}$ subset indicates preeclampsia in said pregnant subject.

2. The method according to claim 1, wherein the level of Siglec-9 on the $CD16^{neg}/CD56^{bright}$ subset is at least 1.5 fold higher than the Siglec-9 on the $CD16^{pos}/CD56^{dim}$ subset.

3. The method according to claim 1, wherein the immune cell sample is a peripheral blood sample.

* * * * *